(12) United States Patent
Dambkowski et al.

(10) Patent No.: US 10,471,235 B2
(45) Date of Patent: Nov. 12, 2019

(54) SYSTEMS AND METHODS FOR PROTECTING UMBILICAL STUMPS

(71) Applicant: The Board of Trustees of the Leland Stanford Junior University, Palo Alto, CA (US)

(72) Inventors: Carl Linden Dambkowski, Palo Alto, CA (US); Eric Fayez Chehab, Mountain View, CA (US); Siddhartha Joshi, Pune (IN); Julie Papanek, San Francisco, CA (US); Jonathan Andrew Fritz, Rancho Santa Fe, CA (US); James Wall, Woodside, CA (US); Ross Daniel Venook, Millbrae, CA (US); Shivani Alexandra Torres, Frisco, TX (US); Joseph De-Chung Shih, Liberty, MO (US); Lauren So Young Wood, Atherton, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 693 days.

(21) Appl. No.: 15/098,286

(22) Filed: Apr. 13, 2016

(65) Prior Publication Data
US 2017/0021134 A1 Jan. 26, 2017

Related U.S. Application Data

(60) Provisional application No. 62/156,120, filed on May 1, 2015, provisional application No. 62/307,396, filed on Mar. 11, 2016.

(51) Int. Cl.
*A61M 25/02* (2006.01)
*A61F 15/00* (2006.01)
*A61F 13/14* (2006.01)

(52) U.S. Cl.
CPC ....... *A61M 25/02* (2013.01); *A61M 2025/024* (2013.01); *A61M 2025/0213* (2013.01);
(Continued)

(58) Field of Classification Search
CPC .............. A61F 13/14; A61F 15/008; A61F 2013/00165; A61F 13/148; A61F 13/00;
(Continued)

(56) References Cited

U.S. PATENT DOCUMENTS

| | | | | |
|---|---|---|---|---|
| 2,652,827 A | * | 9/1953 | Smith | A61F 13/148 128/115.1 |
| 3,674,032 A | * | 7/1972 | Minganti | A61F 13/148 606/120 |

(Continued)

FOREIGN PATENT DOCUMENTS

| CN | 203677702 U | * | 7/2014 |
|---|---|---|---|
| CN | 203677702 U | | 7/2014 |

OTHER PUBLICATIONS

International Search Report & Written Opinion dated Aug. 31, 2016 for PCT Appln. No. PCT/US16/27389.
(Continued)

*Primary Examiner* — Jason E Flick
(74) *Attorney, Agent, or Firm* — Vista IP Law Group, LLP

(57) ABSTRACT

A device for protecting an umbilical stump-catheter interface, includes: a shield having a wall that defines a cavity for accommodating an umbilical stump, wherein the shield further includes a base for attachment to a patient; and an opening at the shield for allowing an umbilical catheter to extend therethrough. A method for protecting an umbilical stump-catheter interface, includes: providing a device having a shield with a wall that defines a cavity for accommodating an umbilical stump, wherein the shield further
(Continued)

includes a base for attachment to a patient, and wherein the device further includes an opening at the shield; shielding the umbilical stump from an environment using the shield; and accommodating an umbilical catheter using the opening at the shield.

77 Claims, 10 Drawing Sheets

(52) U.S. Cl.
CPC ............ *A61M 2025/0246* (2013.01); *A61M 2205/586* (2013.01); *A61M 2205/6063* (2013.01); *A61M 2205/6081* (2013.01); *A61M 2205/7518* (2013.01)

(58) Field of Classification Search
CPC ......... A61F 2013/00089; A61M 25/01; A61M 2025/0213; A61M 2025/024; A61M 2025/0246; A61M 2205/586; A61M 2205/6063; A61M 2205/6081; A61M 2205/7518; A61M 25/02
USPC ........................................................ 604/174
See application file for complete search history.

(56) References Cited

U.S. PATENT DOCUMENTS

| | | | |
|---|---|---|---|
| 4,915,694 A | 4/1990 | Yamamoto et al. | |
| 5,006,830 A * | 4/1991 | Merritt | A61B 17/12 283/75 |
| 5,370,627 A | 12/1994 | Conway | |
| 6,866,652 B2 | 3/2005 | Bierman | |
| 8,269,059 B2 | 9/2012 | Wright | |
| 8,617,115 B2 | 12/2013 | Kennard et al. | |
| 8,641,614 B2 * | 2/2014 | Coelho | A61B 5/0205 600/300 |
| 9,174,027 B2 | 11/2015 | Kennard | |
| 2005/0113759 A1 * | 5/2005 | Mueller, Jr. | A61M 25/02 604/174 |
| 2007/0055205 A1 * | 3/2007 | Wright | A61F 13/023 604/174 |
| 2008/0202531 A1 | 8/2008 | Fletcher | |
| 2010/0179481 A1 | 7/2010 | Bierman et al. | |
| 2010/0228090 A1 | 9/2010 | Weisenburgh et al. | |
| 2011/0282290 A1 | 11/2011 | Kennard et al. | |
| 2012/0232356 A1 | 9/2012 | Coelho | |
| 2014/0060548 A1 * | 3/2014 | Check | A61F 15/008 128/845 |

OTHER PUBLICATIONS

Extended European Search Report dated Dec. 11, 2018 for EP Appln. No. 16789739.6.

\* cited by examiner

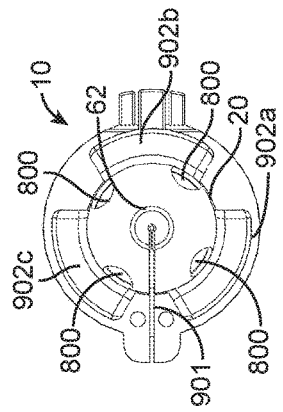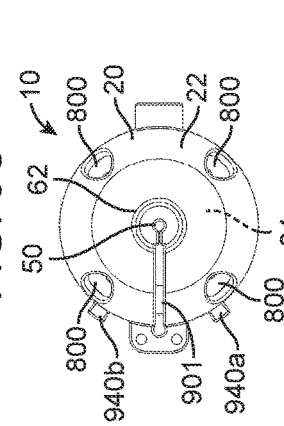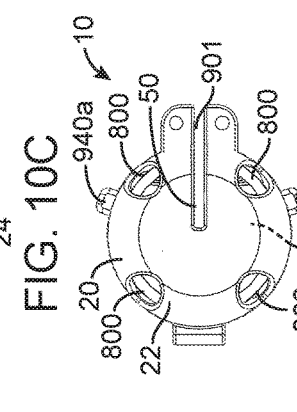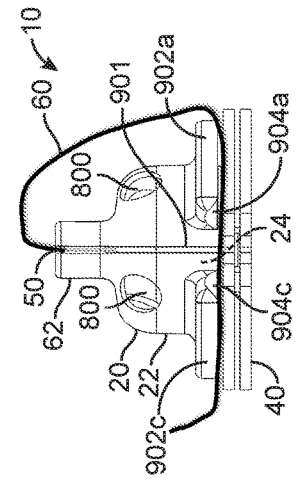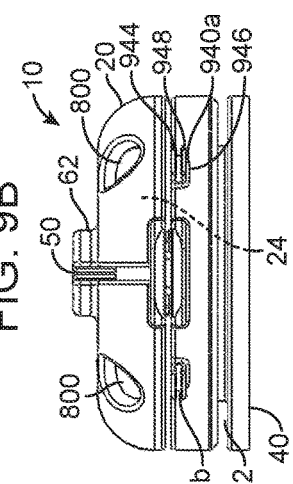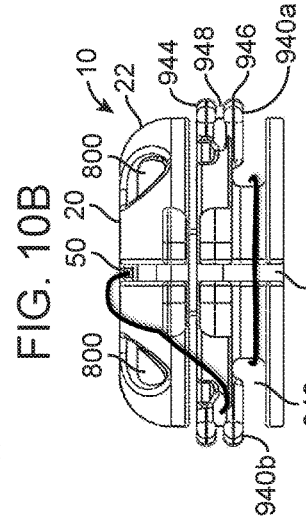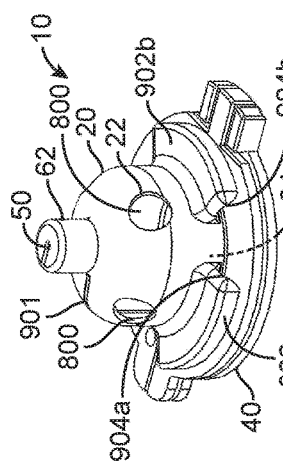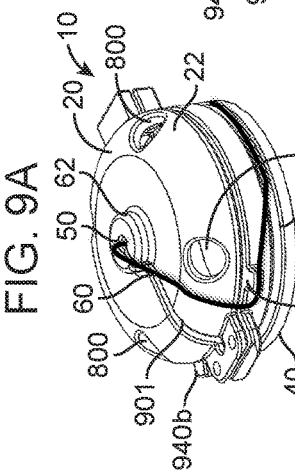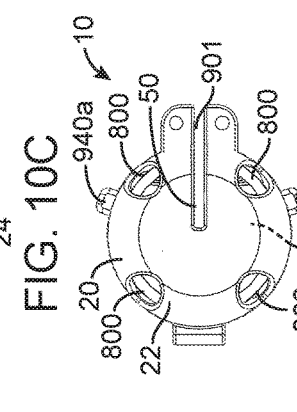

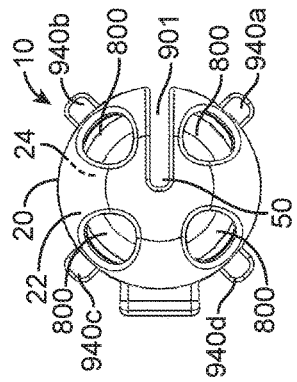
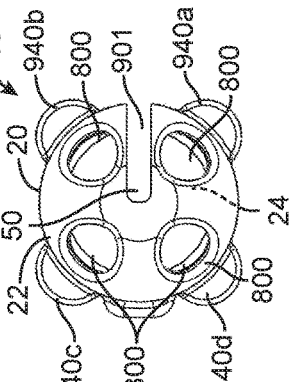
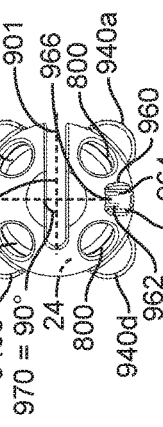
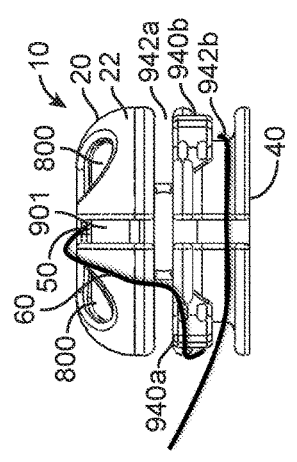
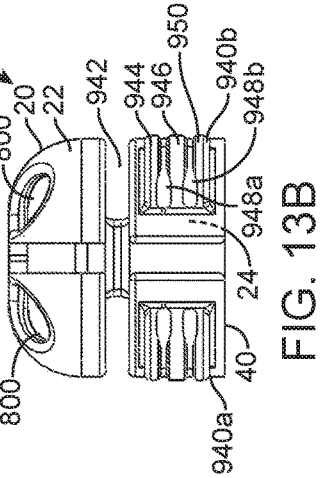
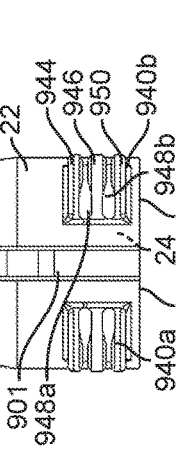
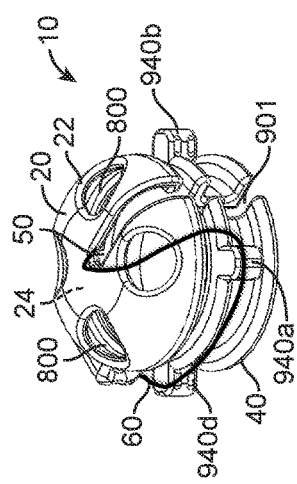
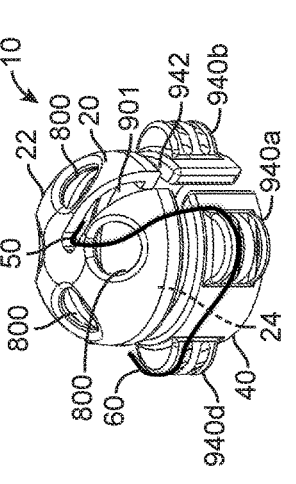
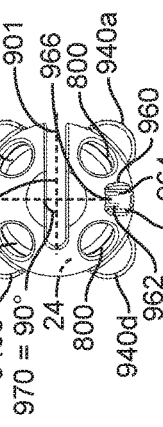

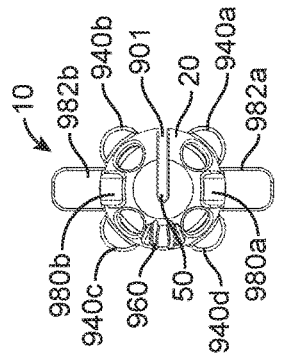
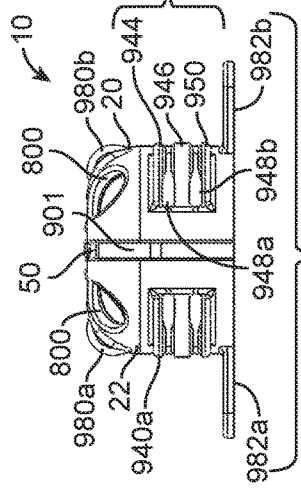
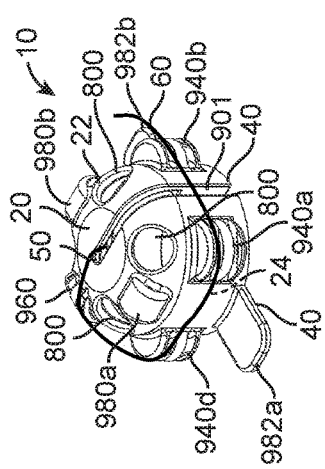
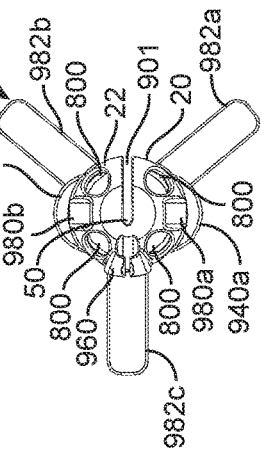
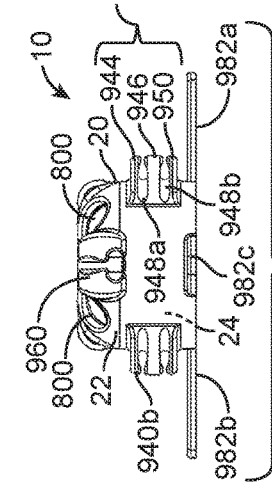
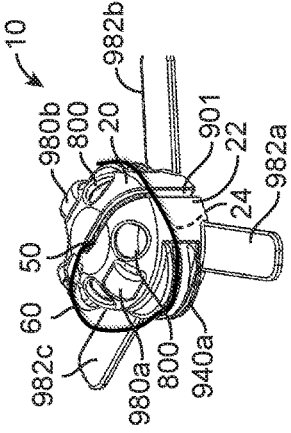
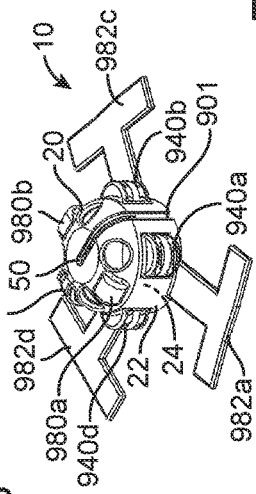

SYSTEMS AND METHODS FOR PROTECTING UMBILICAL STUMPS

RELATED APPLICATION DATA

The application claims priority to, and the benefit of, U.S. Provisional Patent Application No. 62/156,120 filed May 1, 2015, and U.S. Provisional Patent Application No. 62/307,396 filed Mar. 11, 2016. The entire disclosures of both of the above applications are expressly incorporated by reference herein.

FIELD

The field of the application relates to umbilical devices, and more particularly, to systems and methods for protecting umbilical stumps.

BACKGROUND

Every year, more than 5 million central venous catheters (also called central lines) are placed by physicians. Central lines facilitate the delivery of medication and nutritional support to a patient, but can lead to a hospital acquired bloodstream infection. Associated symptoms of central line-associated bloodstream infections (CLABS Is) are sepsis, fever, and malaise. CLABS Is are a major concern for hospitals because they have been associated with increased morbidity and mortality, length of hospital stay, and cost.

Complications associated with low birth weight and premature infants make it necessary for many of these neonates to be admitted to the neonatal intensive care unit (NICU), where a majority of them receives umbilical catheters. Premature infants are particularly vulnerable to bloodstream infections due to their immature immune systems, poor skin integrity, exposure to numerous caregivers, placement in an environment that is conductive to bacterial colonization, and their subjection to repeated invasive procedures. Indeed, the rate of CLABSIs in these infants is far greater than that of adults.

Although umbilical catheterization is a necessary and life-saving procedure for many premature infants, outcomes from CLABSIs can be devastating. Catheter-related bloodstream infections in premature infants are associated with increased morbidity and mortality. Infants with CLABSIs have an increased risk for respiratory distress, severe intraventricular hemorrhage, periventricular leukomalacia, bronchopulmonary dysplasia, and death. CLABSIs are the most common cause of complications related to umbilical catheters, with approximately 5-15% of neonates with umbilical catheters developing CLABSIs. The rate is highest for the lowest birth weight infants, weighing under 1250 grams, who have umbilical catheter CLABSI rates of 15% or more.

Placement of an umbilical catheter is a delicate, multi-step process. First, the cord is elevated vertically and cut approximately one centimeter above the skin with a scalpel blade. Second, the closed tips of forceps are entered into the umbilical vein or artery in order to dilate the vessel. Third, the catheter is introduced into the vessel and advanced 4-5 centimeters. This step may be repeated if the catheter is not properly inserted. Fourth, blood is aspirated to verify catheter placement in the lumen and 0.5 mL of heparin is flushed to clear the lumen. Finally, the catheter is advanced to a predetermined length (based on height and weight of the neonate), attached to the umbilical stump with a suture, and the line is secured with a catheter bridge (sometimes made of surgical tape). Ideal placement of an umbilical venous catheter is at the junction of the inferior vena cava (IVC) and the right atrium of the heart.

Despite high complication risks, umbilical catheters remain the preferred route of catheterization in the NICU because they offer reliable access to the venous system with the necessary flow required to deliver these premature, and often sick, neonates medication, fluids, and parenteral nutrition. Umbilical catheters can also be used to monitor blood pressure and sample venous or arterial blood. With current technologies, physicians remove the umbilical catheter due to risk of CLABSI after approximately 6-8 days, even though there is still typically a need for central access. Indeed, a peripherally inserted central catheter (PICC) line or other form of central catheterization is usually placed in the neonate after UC removal.

Umbilical catheter CLABSIs are at least 5 times more common than central catheter associated bloodstream infections. One possible reason for this is that there is no device that is specific to the unique anatomy of the umbilical area or the unique demands of the neonate that can both protect the umbilical stump and stabilize the umbilical catheter(s).

SUMMARY

A device for protecting an umbilical stump-catheter interface, includes: a shield having a wall that defines a cavity for accommodating an umbilical stump, wherein the shield further includes a base for attachment to a patient; and an opening at the shield for allowing an umbilical catheter to extend therethrough.

Optionally, the opening is at a top of the shield.

Optionally, the opening at the top of the shield extends to a side of the shield.

Optionally, the shield comprises a first clip configured to hold the umbilical catheter.

Optionally, the shield comprises a second clip.

Optionally, the first clip is above the second clip to form a stacked configuration.

Optionally, the first clip and the second clip are disposed at different respective sides of the shield.

Optionally, the first clip is made from a first material having a first durometer, and another part of the shield is made from a second material having a second durometer, the first durometer being higher than the second durometer.

Optionally, the second clip is configured to hold the umbilical catheter or another catheter.

Optionally, the first clip has a first catheter slot, the second clip has a second catheter slot, the first catheter slot having a dimension that is different from a dimension of the second catheter slot.

Optionally, the device further includes a third clip, wherein the first clip is configured to hold the umbilical catheter, the second clip is configured to a first additional catheter, and the third clip is configured to hold a second additional catheter or the umbilical catheter.

Optionally, the first clip and the second clip are integrated as a single component.

Optionally, the shield comprises a first portion having a first durometer, and a second portion having a second durometer, the first durometer being higher than the second durometer.

Optionally, the shield comprises one or more spooling grooves at one or more sides of the shield, the one or more spooling grooves configured to accommodate a segment of the umbilical catheter.

Optionally, the shield comprises a circumferentially disposed spooling groove configured to accommodate a segment of the umbilical catheter.

Optionally, the shield has a top portion, and wherein the shield further comprises a clip at the top portion for holding and/or guiding the umbilical catheter.

Optionally, the shield has a top portion, and wherein the shield further comprises at least two pinching protrusions at the top portion for allowing a user to grasp the shield.

Optionally, the shield comprises an exterior surface configured for allowing a user to write on.

Optionally, the shield comprises a color coding or a labeling.

Optionally, the base comprises a T-shape portion, a linear portion, or a curvilinear portion, or a full circumferential portion, extending away from a side of the shield.

Optionally, the shield has a first shield portion and a second shield portion that is moveably coupled to the first shield portion, wherein when the second shield portion is in a first position, the umbilical stump is shielded by the shield, and when the second shield portion is in a second position, the umbilical stump is exposed to an environment outside the shield.

Optionally, the device further includes a mechanical hinge for rotatably coupling the second shield portion to the first shield portion.

Optionally, the second shield portion is moveable relative to the first shield portion in a plane that is parallel to the base.

Optionally, the device further includes a securing device for locking the second shield portion relative to the first shield portion when the second shield portion is in the first position.

Optionally, the device further includes a seal located at or adjacent the opening, the seal having a first seal portion that is coupled to the first shield portion, and a second seal portion that is coupled to the second shield portion.

Optionally, at least a part of the shield has a dome shape.

Optionally, the device further includes a tubular structure extending from the dome shape shield, wherein the tubular structure has a channel that extends from the opening.

Optionally, the tubular structure is at a top of the dome shape shield.

Optionally, the device further includes a seal located at or adjacent the opening.

Optionally, the seal has a first seal portion and a second seal portion that cooperates with the first seal portion for securing the umbilical catheter relative to the device.

Optionally, a majority of the shield is rigid.

Optionally, the shield is non-rigid, and is collapsible in response to a compress force that is less than 1 lb.

Optionally, the device further includes an adhesive at the base for attaching the base to the patient.

Optionally, the base includes one or more openings or slots for providing suction.

Optionally, the device further includes a spring-loaded device for securing the umbilical catheter relative to the device.

Optionally, at least a part of the shield is transparent.

Optionally, the device further includes a seal for mechanically holding the umbilical catheter, wherein the seal is configured to protect the umbilical stump from bacteria associated with the umbilical catheter.

Optionally, the shield is configured to protect the umbilical stump from bacteria outside the shield and/or from physical contact.

Optionally, the shield comprises a vent for allowing some air exchange through the wall of the shield.

Optionally, the device further includes a permeable or semipermeable cover covering the vent.

Optionally, the device further includes a cover that can be selectively opened to expose the vent or closed to shut the vent.

Optionally, the opening is at a side of the shield.

Optionally, the opening is at an upper portion of the shield and is offset from a center of the shield.

Optionally, the base, or an entirety, of the shield includes an antimicrobial material.

Optionally, the device further includes an ultraviolet light source coupled to the shield.

Optionally, the shield has a width that is less than 5 inches.

Optionally, the device further includes a manual control mechanism configured to shut the umbilical catheter so that fluid flow in the umbilical catheter can be stopped.

Optionally, the device further includes a position monitoring device for monitoring a position of the umbilical catheter with respect to the shield, to the patient, or to the umbilical stump.

A kit includes: the device as described previously; and one or a combination of two or more of: a scissor, a scalpel, a stopcock, a syringe, a measuring tape, a dilator, a needle, a sterilization material, a catheter, a drape, a sponge, a suture, an umbilical tie, an anesthetic agent, a forceps, a needle holder, a hemostat, a syringe, a bag of sterile saline, and a gauze pad.

Optionally, the kit further includes a container having a compartment for housing the device, and one or more additional compartment(s) for housing the scissor, the scalpel, the stopcock, the syringe, the measuring tape, the dilator, the needle, the sterilization material, the catheter, the drape, the sponge, the suture, the umbilical tie, the anesthetic agent, the forceps, the needle holder, the hemostat, the syringe, the bag of sterile saline, the gauze pad, and any combination of two or more of the foregoing.

A method for protecting an umbilical stump-catheter interface, includes: providing a device having a shield with a wall that defines a cavity for accommodating an umbilical stump, wherein the shield further includes a base for attachment to a patient, and wherein the device further includes an opening at the shield; shielding the umbilical stump from an environment using the shield; and accommodating an umbilical catheter using the opening at the shield.

Optionally, the device further includes a seal at or adjacent the opening, and wherein the method further comprises protecting the umbilical stump from bacterial associated with the umbilical catheter using the seal.

Optionally, the method further includes stabilizing the umbilical catheter with respect to the device by detachably securing the umbilical catheter to the device.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

FIG. 9A illustrates a perspective view of another device for protecting an umbilical stump-catheter interface.

FIG. 9B illustrates a side view of the device of FIG. 9A, particularly showing the device being used with a catheter.

FIG. 9C illustrates a top view of the device of FIG. 9A.

FIG. 10A illustrates a perspective view of another device for protecting an umbilical stump-catheter interface, particularly showing the device being used with a catheter.

FIG. 10B illustrates a side view of the device of FIG. 10A.

FIG. 10C illustrates a top view of the device of FIG. 10A.

FIG. 11A illustrates a perspective view of another device for protecting an umbilical stump-catheter interface, particularly showing the device being used with a catheter.

FIG. 11B illustrates a side view of the device of FIG. 11A.

FIG. 11C illustrates a top view of the device of FIG. 11A.

FIG. 12A illustrates a perspective view of another device for protecting an umbilical stump-catheter interface, particularly showing the device being used with a catheter.

FIG. 12B illustrates a side view of the device of FIG. 12A.

FIG. 12C illustrates a top view of the device of FIG. 12A.

FIG. 13A illustrates a perspective view of another device for protecting an umbilical stump-catheter interface, particularly showing the device being used with a catheter.

FIG. 13B illustrates a side view of the device of FIG. 13A.

FIG. 13C illustrates a top view of the device of FIG. 13A.

FIG. 14A illustrates a perspective view of another device for protecting an umbilical stump-catheter interface, particularly showing the device being used with a catheter.

FIG. 14B illustrates a side view of the device of FIG. 14A.

FIG. 14C illustrates a top view of the device of FIG. 14A.

FIG. 15A illustrates a perspective view of another device for protecting an umbilical stump-catheter interface, particularly showing the device being used with a catheter.

FIG. 15B illustrates a side view of the device of FIG. 15A.

FIG. 15C illustrates a top view of the device of FIG. 15A.

FIG. 16A illustrates a perspective view of another device for protecting an umbilical stump-catheter interface, particularly showing the device being used with a catheter.

FIG. 16B illustrates a side view of the device of FIG. 16A.

FIG. 16C illustrates a top view of the device of FIG. 16A.

FIG. 17 illustrates another device for protecting an umbilical stump-catheter interface.

FIG. 18 illustrates another device for protecting an umbilical stump-catheter interface.

DETAILED DESCRIPTION

Figure 1:
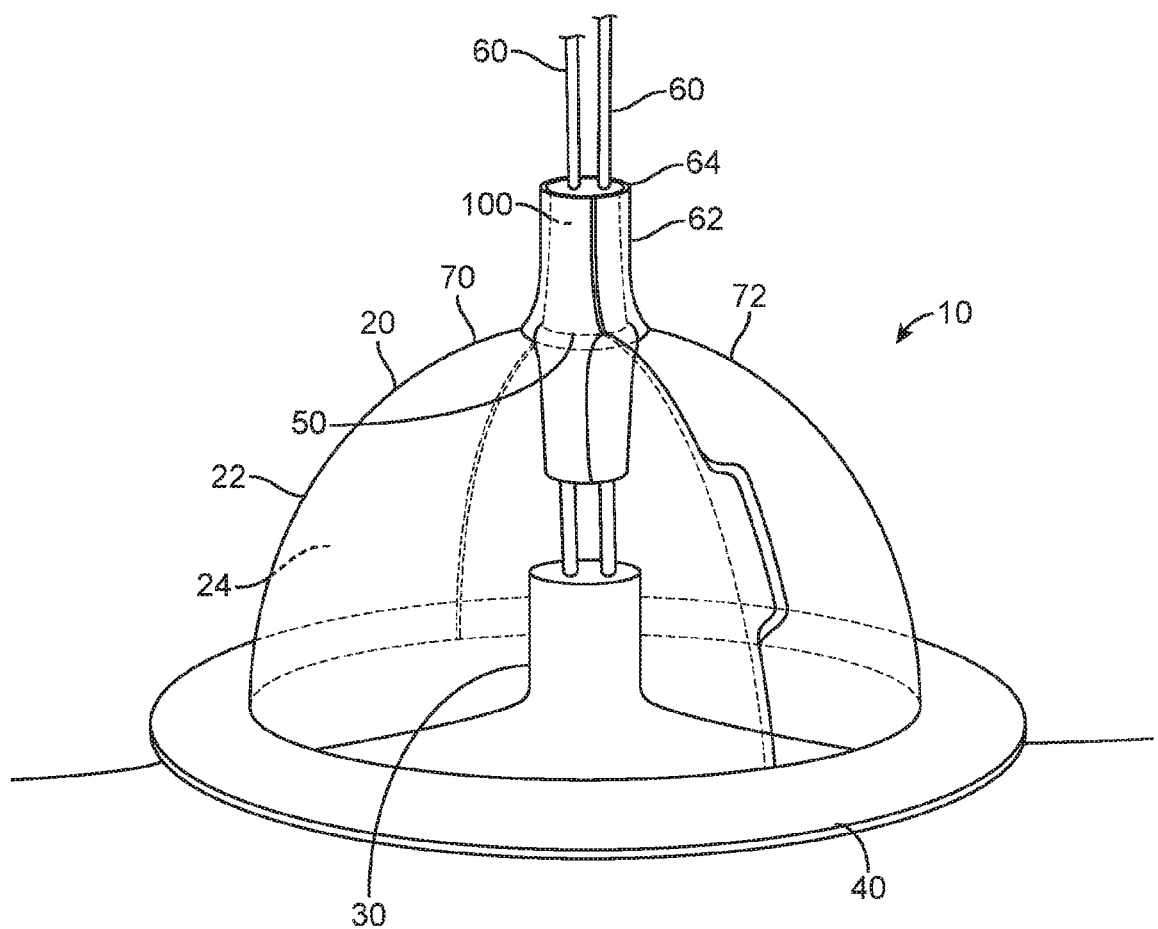
FIG. 1 illustrates device for protecting an umbilical stump-catheter interface.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

In at least one embodiment, a device for protecting an umbilical stump is provided. The device may be used to protect an umbilical stump after umbilical catheterization. The device may also be used to secure, and optionally seal against, the umbilical catheter in order to reduce the risk of a central-line associated bloodstream infection. In one implementation, the device is a rigid, plastic device that covers and isolates a small area around the umbilical catheter insertion site from the surrounding environment, and effectively halts bacterial migration to this area. The device also has an adhesive seal at the base of the device for preventing migration of bacteria from the skin into the stump.

FIG. 1 illustrates a device 10 for protecting an umbilical stump-catheter interface. The device 10 has a shield 20 with a wall 22 that defines a cavity 24 for accommodating an umbilical stump 30. As shown in the figure, the shield 20 further includes a base 40 for attachment to a patient (e.g., a neonate). The device 10 also has an opening 50 at the shield 20 for allowing one or more umbilical catheter(s) 60 to extend therethrough.

In the illustrated embodiments, at least a part of the shield 20 has a dome shape. In particular, the bottom portion of the shield 20 has a dome shape, while a top portion of the shield 20 has a tubular structure 62. In other embodiments, the tubular structure 62 may be considered to be a separate component from the shield 20 (regardless of whether they are formed together or separately attached to each other). In such cases, the entirety of the shield 20 may be considered as having a dome shape. As shown in the figure, the tubular structure 62 extends from the dome shape shield 20, and has a channel 64 that extends from the opening 50. The tubular structure 62 is at a top of the dome shape shield 20. In other embodiments, the tubular structure 62 may be extending from the dome shape shield 20 at other locations of the dome shape shield 20.

In other embodiments, the shield 20 may not have a dome shape. For example, in other embodiments, the shield 20 may have a rectangular box shape, a square box shape, a pyramid shape, a cylindrical shape, or any of other shapes.

Also, in other embodiments, the tubular structure 62 may not extend outward from the shield 20. For example, in other embodiments, the tubular structure 62 (or at least a part of it) may extend inward into the cavity 24 defined by the shield 20.

In the illustrated embodiments, the shield 20 has a first shield portion 70 and a second shield portion 72 that is moveably coupled to the first shield portion 70. When the second shield portion 72 is in a first position, the umbilical stump 30 is shielded by the shield 20 (see FIGS. 1 and 2B), and when the second shield portion 72 is in a second position, the umbilical stump 30 is exposed to an environment outside the shield 20 (see FIG. 2A).

In the illustrated embodiments, the first shield portion 70 of the shield 20 is rigid, and the second shield portion 72 of the shield 20 is also rigid. In other embodiments, a part of the shield 20 may be flexible. For example, in other embodiments, the base 40 of the shield 20 may be flexible. In some cases, the base 40 may be made from a polymer or a plastic. Also, in some embodiments, a majority of the shield 20 is rigid. Furthermore, in some embodiments, the base 40 may be made from a material that is more flexible compared to the shield 20. A flexible base 40 has the advantageous of allowing the base to conform with a surface profile of a skin of the patient. In addition, in the illustrated embodiments, at least a part of the shield 20 is transparent. This feature allows a physician or a nurse to see the condition of the umbilical stump 30, the stump-catheter interface, the catheter coming out from the stump 30, position of catheter, and catheter marking (if any).

Figure 2A:
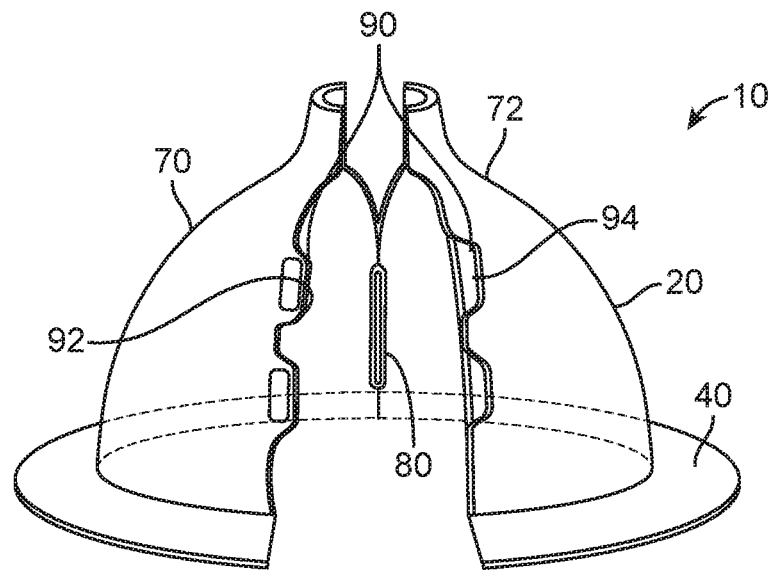
FIGS. 2A-2B illustrate a shield of the device of FIG. 1, particular showing the shield having an open-configuration and a closed-configuration.
Figure 2B:
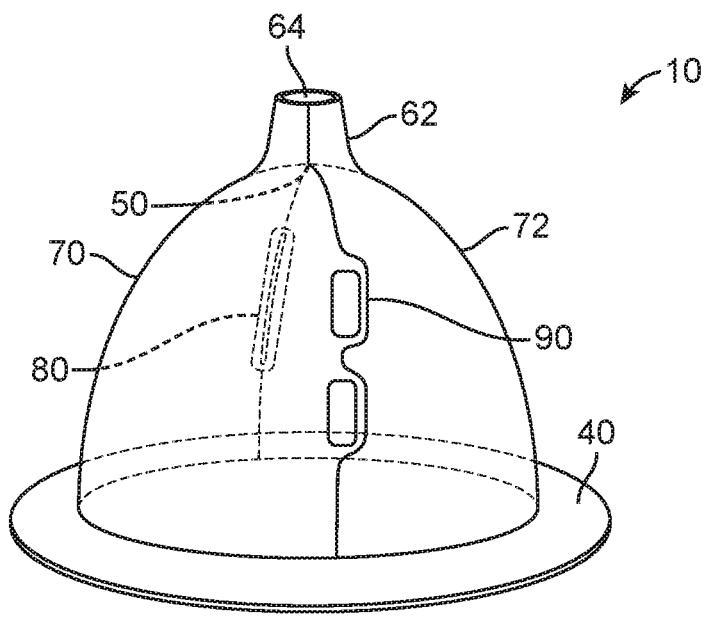

Also, as shown in FIGS. 2A-2B, the device 10 has a mechanical hinge 80 for rotatably coupling the second shield portion 72 to the first shield portion 70. In some cases, the hinge 80 may be implemented using a connection rod. In other embodiments, the hinge 80 may be implemented using a flexible plastic that is connected between the first shield portion 70 and the second shield portion 72. The hinge 80 may be a double-action hinge, a live hinge, etc. The second shield portion 72 is moveable relative to the first shield portion 70 in a path that is parallel to a plane of the base 40. In other embodiments, the second shield portion 72 may be moveable relative to the first shield portion 70 in a path that is non-parallel to a plane of the base 40.

Also, in the illustrated embodiments, the device 10 further includes a securing device 90 for locking the second shield portion 72 relative to the first shield portion 70 when the second shield portion 72 is in the first position. In some cases, the securing device 90 may be a snap-fit connector. For example, the first shield portion 70 may have one or more loops 92, and the second shield portion 72 may have one or more corresponding anchors 94 for snap-fit into the respective loop(s) 92. With this configuration, the first and second shield portions 70, 72 can snap close, and may be pulled open relative to each other by applying a small push at the area next to the anchor(s). In other embodiments, the securing device 90 may be any of other types of connection mechanism, such as a Velcro, an interference-fit connector, a button, etc.

Figure 3A:
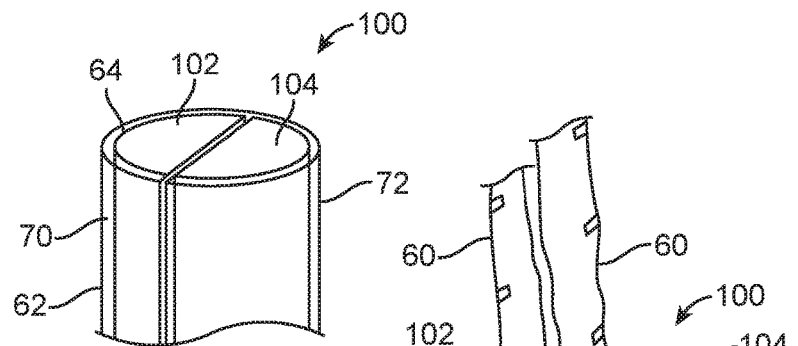
FIG. 3A illustrates a catheter seal.
Figure 3B:
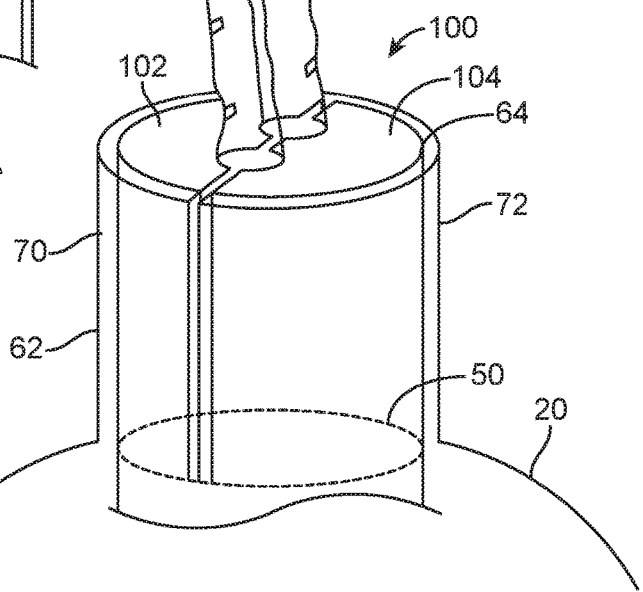
FIG. 3B illustrates the catheter seal of FIG. 3A, with two umbilical catheters placed between two seal portions.

As shown in FIGS. 1, 3A, and 3B, the device 10 also includes a seal 100 located at or adjacent the opening 50 (note that the seal 100 is not shown in FIGS. 2A-2B for clarity). In particular, as shown in FIG. 3A, the seal 100 is located within the channel 64 in the tubular structure 62. The seal 100 has a first seal portion 102 that is coupled to the first shield portion 70 (or to a first part of the tubular structure 62), and a second seal portion 104 that is coupled to the second shield portion 72 (or to a second part of the tubular structure 62). The first seal portion 102 and the second seal portion 104 are configured to cooperate with each other for securing the umbilical catheter 60 relative to the device 10. In particular, the seal 100 is configured for mechanically holding the umbilical catheter 60 in a vertical position like that shown in FIG. 3B. In other embodiments, the seal 100 may be configured to hold the umbilical catheter 60 at other orientations relative to the patient. For example, in other embodiments, the tubular structure 62 with the seal 100 may be oriented horizontally or at an acute angle relative to a vertical axis.

In some embodiments, the material and/or the size and shape of the seal 100 can be selected so that the resulting seal 100 can provide a desired frictional force that impedes catheter movement relative to the seal 100, while providing a compliance that does not collapse or over-compress the catheter (to impede fluid flow). Accordingly, in some embodiments, the closing of the seal portions 102, 104 functions to secure the catheter relative to the seal 100. Also, in some cases, the longitudinal dimension of the seal (i.e., along the direction of the catheter) can be increased to further improve contact area between the seal 100 and the catheter.

As discussed, the seal 100 may be at or adjacent the opening 50. In some cases, the seal 100 may be considered as being "at" the opening 50 if any part of the seal 100 intersects a cross section of the opening 50. Also, in some cases, no part of the seal 100 intersects a cross section of the opening 50. In such cases, the seal 100 may be considered to be "adjacent" the opening 50 if a spacing between the seal 100 and the opening 50 (measured along a longitudinal axis of the tubular structure 62) is less than 3 cm, and more preferably less than 1 cm.

In one implementation, the first seal portion 102 and the second seal portion 104 may be made from rubber (e.g., neoprene rubber). The first seal portion 102 and the second seal portion 104 may have a shore hardness of 70 that allows the seal portions 102, 104 to deform around the catheter(s) 60. This secures the catheter(s) 60 without occluding them due to compression by the seal portions 102, 104. In other embodiments, the seal portions 102, 104 may have other hardness. As shown in FIG. 3A, before the seal portions 102, 104 are used to clamp around the catheter(s) 60, the seal portions 102, 104 have respective surfaces that face towards each other, wherein the surfaces are planar. When one or more catheter(s) 60 are placed between the seal portions 102, 104, and when the seal portions 102, 104 are used to grip around the catheter(s) 60, the opposing surfaces of the seal portions 102, 104 deform around the catheter(s) 60 (see FIG. 3B). Such configuration is advantageous because it allows the seal 100 to form a physical barrier to prevent bacteria from outside the device 10 to travel into the cavity 24. Such configuration is also advantageous because it allows the seal 100 to stabilize different sized catheters. In other embodiments, instead of the opposing planar surfaces that deform in response to placement of the catheter(s) there between, the seal portions 102, 104 may have one or more pre-formed channels for accommodating respective catheter(s) 60.

Also, in some embodiments, the seal portions 102, 104 may have a sufficiently high friction that allows the seal portions 102, 104 to prevent movement of the catheter(s) 60 when the seal portions 102, 104 are closed around the catheter(s) 60. In some cases, the friction may be sufficient to prevent self-movement between the catheter(s) 60 and the seal 100, while allowing a physician to manually slide the seal 100 relative to the catheter(s) 60. In other embodiments, the friction may be sufficiently high to prevent a physician from manually sliding the seal 100 relative to the catheter(s) 60.

In the illustrated embodiments, the seal 100 is configured to protect the umbilical stump 30 from bacteria associated with the umbilical catheter 60, while the shield 20 is configured to protect the umbilical stump 30 from bacteria from environment outside the shield 20.

Figure 4:
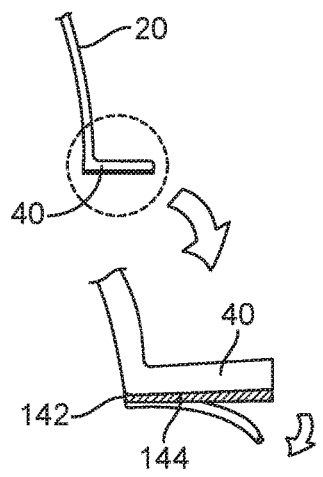
FIG. 4 illustrates a base of a shield.

As shown in FIG. 4, the device 10 also includes an adhesive 142 at the base 40 for attaching the base 40 to the patient. In one implementation, the adhesive 142 may be a double-sided tape, with a first side attached to a bottom surface of the base 40, and a second side (opposite from the first side) facing downward. The device 10 may also include a tape cover 144 covering the second side of the adhesive 142. Since a neonate's skin is particularly sensitive to irritation and damage, the strength and chemical composition of the adhesive 142 may be designed to protect the neonate's skin. In one implementation, a hydrocolloid gel may be used to implement the adhesive 142. Such an adhesive may have minimal skin irritation over a long period of time.

Figure 5:
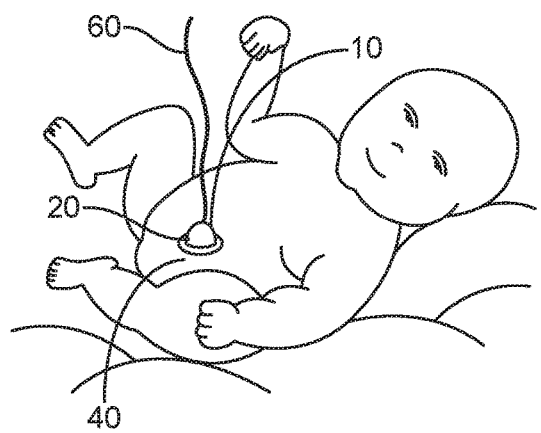
FIG. 5 illustrates a method of using the device of FIG. 1.

FIG. 5 illustrates a method of using the device 10. First, the device 10 is provided. As discussed, the device 10 includes a shield 20 with a wall 22 that defines a cavity 24 for accommodating an umbilical stump 30, wherein the shield 20 further includes a base 40 for attachment to a patient. In some embodiments, the act of providing the device 10 may be performed by a manufacturer of the device 10. In other embodiments, the act of providing the device 10 may be performed by an importer of the device 10. In further embodiments, the act of providing the device 10 may be performed by a distributer, a hospital, a physician, or a nurse.

Before the device 10 is used to shield the umbilical stump 30, the adhesive tape 144 is removed from the adhesive 142 (see FIG. 4). After the bottom surface of the adhesive 142 is exposed, the shield 20 is then placed over the umbilical stump 30, and the base 40 of the shield 20 is then attached to the patient using the adhesive 142. In some embodiments, as the base 40 is being attached to the patient, the first shield portion 70 and the second shield portion 72 are closed relative to each other, thereby closing the first and second seal portions 102, 104 towards the umbilical catheter 60. In other embodiments, the first shield portion 70 and the second shield portion 72 may be closed relative to each other first, to thereby close the seal portions 102, 104 to grip the umbilical catheter 60. The shield 20 is then moved down towards the patient's skin to secure the base 40 on the patient's skin. As the shield 20 is moved down, the seal portions 102, 104 surrounding the umbilical catheter 60 slide relative to the umbilical catheter 60 while the umbilical catheter 60 is confined within the space defined between the seal portions 102, 104.

In the illustrated embodiments, the opening 50 at the shield 20 allows the umbilical catheter 60 to extend through the shield 20 while the umbilical catheter 60 is gripped between the seal portions 102, 104. Accordingly, the opening 50 at the shield 20 accommodates the umbilical catheter 60.

After the shield 20 is placed around the umbilical stump 30, the umbilical stump 30 is then shielded from an environment using the shield 20. The seal 100 formed by the seal portions 102, 104 also protects the umbilical stump 30 from bacterial associated with the umbilical catheter 60. In addition, the adhesive 142 at the base 40 prevents bacteria at the skin outside the shield 20 from reaching the umbilical stump 30.

As shown in the above embodiments, the device 10 is advantageous because (1) it isolates the area around the catheter insertion site from surrounding environment to prevent or at least reduce bacterial migration to this area from the air, (2) its adhesive 142 below the base 40 functions as a seal that prevents or at least reduce migration of bacteria from the skin into the umbilical stump and attaches the device 10 to the skin, and (3) the seal 100 secures the catheter(s) 60 relative to the shield 20 and prevents or at least reduce bacterial migration from the catheter(s) 60 into the umbilical stump. These benefits would lead to a reduction in neonate morbidity and mortality, would increase the ease of neonate care in the NICU, and may reduce cost of care. Also, the device 10 is advantageous because it does not interfere with current umbilical catheterization procedures. This allows the integration of the device 10 into current practice easy. The device 10 is also easy to use.

Figure 6:
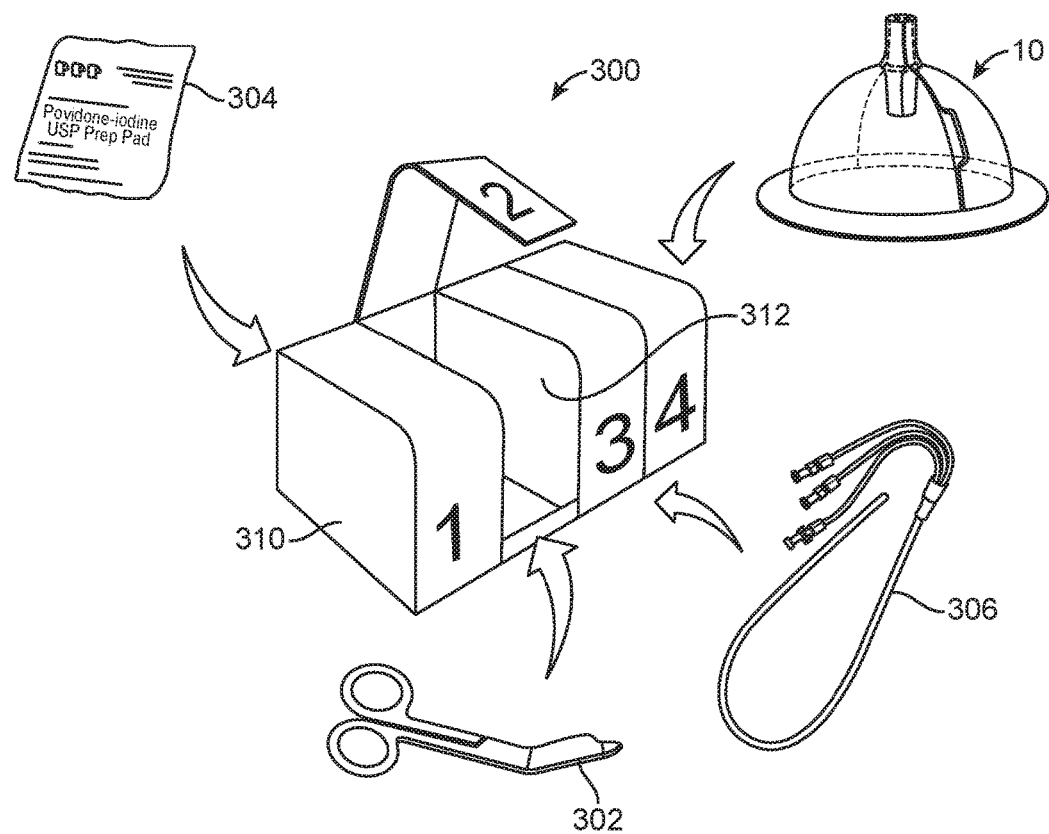
FIG. 6 illustrates a kit that includes the device of FIG. 1.

In one or more embodiments described herein, the device 10 for protecting the umbilical stump-catheter interface may be a part of a kit. FIG. 6 illustrates a kit 300 that includes the device 10. In the illustrated embodiments, the kit 300 also includes a scissor 302, one or more sterilization material(s) 304, and one or more umbilical catheters 306. By means of non-limiting examples, a sterilization material may be chlorhexidine, betadine, etc. The kit 300 also includes a container 310 having a plurality of compartments 312 for housing the device 10, the scissor 302, the one or more sterilization materials 304, and the one or more umbilical catheters 306, respectively. It should be noted that the kit 300 is not limited to the configuration shown, and that the kit 300 may have other configurations in other embodiments. For example, in other embodiments, instead of having all of the items shown, the kit 300 may include the device 10, and one or a combination of: a scissor, a sterilization material, and an umbilical catheter. In other embodiments, instead of only having the items aforementioned, the kit 300 may include additional materials. The kit 300 is advantageous because it provides an integrated solution. In particular, the kit 300 may include tools that are involved in the placement of umbilical catheter, and also the device 10 for protecting the umbilical stump 30. During use, the physician or nurse can use the sterilization material 304 in the kit 300 for disinfection of a treatment site. After the treatment site at the patient has been disinfected, the physician or nurse can then apply the umbilical catheter 306 in the kit 300 on the patient. If any cutting is needed in the process, the physician or nurse can also use the scissor 302 in the kit 300. Furthermore, the physician or nurse can use the device 10 in the kit 300 to shield and protect the umbilical stump against bacterial infection associated with the catheter and/or the environment surrounding the patient (e.g., by preventing the umbilical stump from being in physical contact with objects and/or substances outside the shield).

It should be noted that the kit 300 is not limited to having the above items, and that the kit 300 may include other items in other embodiments. For example, in other embodiments, in addition to including the device 10, the kit 300 may include one or a combination of: a scissor, a scalpel, a stopcock, a syringe, a measuring tape, a dilator, a needle, a sterilization material, a catheter, a drape, a sponge, a suture, an umbilical tie, an anesthetic agent, a forceps, a needle holder, a hemostat, a syringe, a bag of sterile saline, and a gauze pad. Also, the container 310 of the kit 300 may have a compartment for housing the device 10, and one or more additional compartment(s) for housing one or a combination of: a scissor, a scalpel, a stopcock, a syringe, a measuring tape, a dilator, a needle, a sterilization material, a catheter, a drape, a sponge, a suture, an umbilical tie, an anesthetic agent, a forceps, a needle holder, a hemostat, a syringe, a bag of sterile saline, and a gauze pad.

Figure 7:
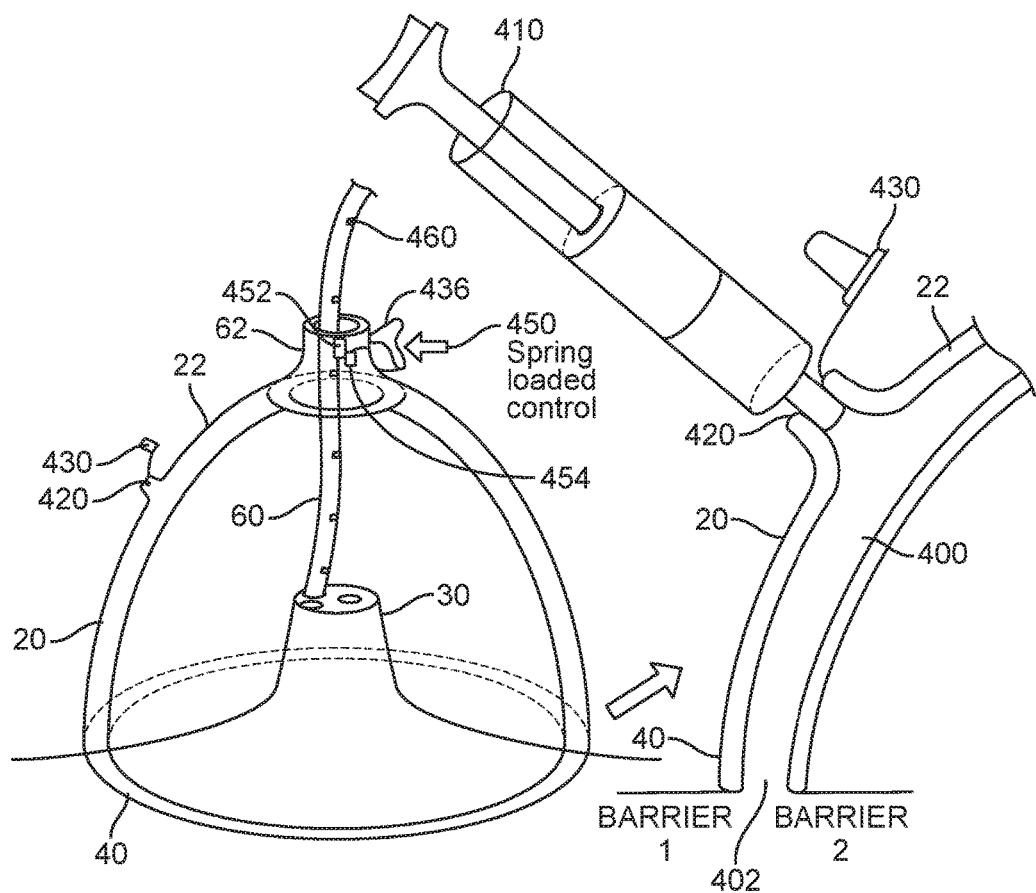
FIG. 7 illustrates another device for protecting an umbilical stump-catheter interface.

It should be noted that the device 10 should not be limited to the examples described above, and that the device 10 may have other configurations in other embodiments. For example, as shown in FIG. 7, in other embodiments, instead of, or in addition to, using the adhesive 142, the shield 20 of the device 10 may include a channel 400 within the wall 22 of the shield 20. The channel 400 may be defined by the wall 22 of the shield 20. Alternatively, the channel 400 may be in a separate tube that is located inside the wall of the shield 20. The channel 400 is in fluid communication with opening(s) or slot(s) 402 at the bottom (base 40) of the shield 20 where the shield 20 interfaces with the skin of the patient. During use, a syringe 410 may be coupled to an opening 420 at the wall 22 of the shield 20, and the syringe 410 may then be used to apply suction inside the channel 400. The suction causes the patient's skin to be pulled towards the opening(s) or slot(s) 402 at the bottom of the shield 20, thereby securing the skin relative to the shield 20. After sufficient suction has been applied, a cover 430 may then be used to cover up the opening 420.

In some cases, the opening 420 may include a one-way valve. This allows the syringe 410 to remove air within the channel 400 in one direction to create suction within the channel 400, and after the syringe 410 is removed from the opening 420, air will not leak back into the channel 400. If the device 10 is to be decoupled from the patient, the device 10 may be pulled away from the skin, or the patient skin next to the base 40 may be pressed, thereby allowing air to leak back into the channel 400. In further embodiments, a pin or a rod may be inserted into the one-way valve in the opening 420 to open up the valve, thereby allowing air to leak back into the channel 400 to remove the suction.

Also, in one or more embodiments described herein, instead of using the seal 100, the device 10 may include a spring-loaded device 450 (like that shown in FIG. 7) at the tubular structure 62, for securing the catheter 60 relative to the device 10. The spring-loaded device 450 may include an engagement member 452 located inside the channel 64 of the tubular structure 62, and a spring 454 for biasing the engagement member 452 to push the engagement member 452 into the channel 64 inside the tubular structure 62. When the catheter 60 is placed inside the channel 64, the user may pull the tap 456 at the spring-loaded device 450 to allow the catheter 60 to be inserted into the channel 64. When the catheter 60 is desirably positioned relative to the tubular structure 62, the tap 456 may then be released to allow the engagement member 452 to be pushed by the spring 454 towards the catheter 60 to thereby secure the catheter 60 in place. In some cases, the engagement member 452 may be a pin, and the catheter 60 may have multiple openings/indentations 460, wherein the pin may be selectively placed into a one of the openings/indentations 460. In other embodiments, the catheter 60 may have a smooth surface, and the engagement member 452 may be configured to secure the catheter 60 by friction.

In one or more embodiments described herein the shield 20 may optionally further include one or more vents. FIG. 8A illustrates an embodiment of the shield 20, particularly showing the shield 20 having multiple vents 800. The vents 800 may be advantageous in that they may prevent a "bio-dome" like effect (which may cause an increase of bacterial load) within the cavity of the shield 20. Also, the vent(s) 800 may allow umbilical stump to dry and prevent further bacterial growth. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800. Also, in some embodiments, the shield 20 may include vents with different sizes, or vents with the same size. In further embodiments, the vents may include respective covers that may be selectively opened or closed, thereby allowing a user to selectively choose to allow more air flow or air exchange across the shield 20. Each cover may be in a form of a door that is rotatably coupled to the shield 20 that can be opened or closed to shut the vent. Alternatively, each cover may be in a form of a tape, that may be selectively peeled off by the user to open the vent.

Also, in other embodiments, the vents 800 at the shield 20 may be larger than those show in FIG. 8A. For example, as shown in FIG. 8B, in other embodiments, the shield 20 may have relatively larger vents 800.

In addition, in the illustrated embodiments, the vents 800 at the shield 20 all have the same size. In other embodiments, at least two of the vents 800 at the shield 20 may be in different sizes.

Figure 8C:
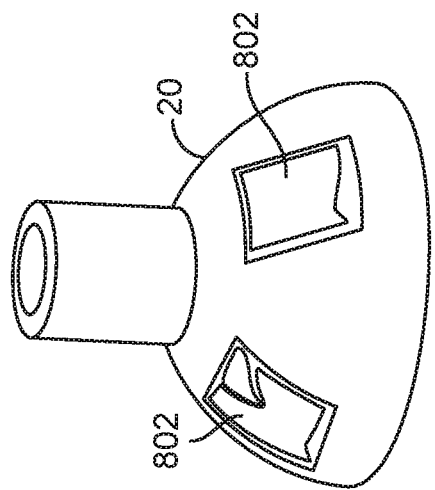
FIGS. 8A-8C illustrate different shields in different embodiments.
Figure 8B:
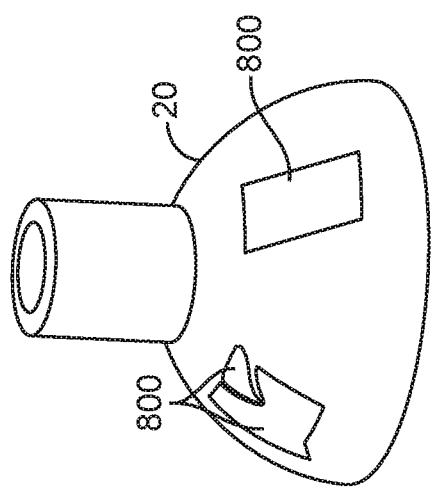
Figure 8A:
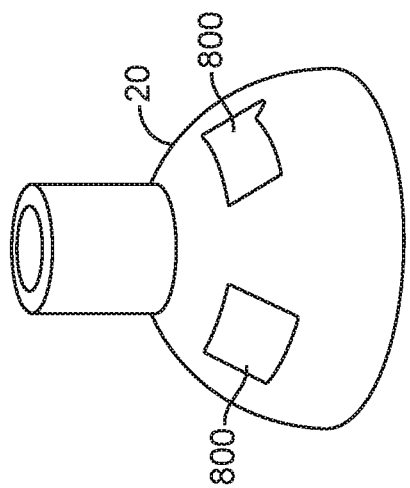

Furthermore, as shown in FIG. 8C, in other embodiments, the vent(s) 800 at the shield 20 may be covered by permeable or semipermeable cover(s) 802. The cover(s) 802 is advantageous because it further limits an amount of air exchange and/or bacterial entry through the wall of the shield 20.

It should be noted that the device 10 is not limited to having the above configurations and features, and that the device 10 may have other configurations and features in other embodiments.

For example, FIGS. 9A-9C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. The shield 20 has a tubular structure 62 at the top of the shield, which functions as a stabilizer to stabilize the umbilical catheter 60 while the umbilical catheter 60 is accommodated in the opening 50. In other embodiments, the shield 20 may not include the tubular structure 62. As shown in the figures, the opening 50 is located at a top of the shield 20, and extends to a side of the shield 20, thereby defining a linear slot 901 at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump. Also, the above configuration is advantageous because it allows the catheter 60 to exit from the opening 50 at any angle relative to the shield 20.

The shield 20 also has multiple vents 800. The vents 800 may prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a first portion 902a, a second portion 902b, and a third portion 902c disposed at different respective sides of the shield 20. The portions 902a-902c define respective slots 904a-904c for accommodating the umbilical catheter 60 when the umbilical catheter 60 is wrapped around the shield 20. As shown in the figures, each of the portions 902a-902c has a first cross section at an outermost radial distance from a center of the shield 20, and a second cross section that is smaller than the first cross section at a radial distance that is closer to the center of the shield 20. This configuration forms an anchor to reduce the risk that the umbilical catheter 60 will move radially outward and unwrap itself from the shield 20. Although three portions 902a-902c are shown, in other embodiments, the device 10 may include only a single portion 902, two portions 902, or more than three portions 902.

FIGS. 10A-10C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. The shield 20 has a tubular structure 62 at the top of the shield, which functions as a stabilizer to stabilize the umbilical catheter 60 while the umbilical catheter 60 is accommodated in the opening 50. In other embodiments, the shield 20 may not include the tubular structure 62. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

The shield 20 also has multiple vents 800. The vents 800 may prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a, 940b disposed at different respective sides of the shield 20. The clips 940a, 940b are configured to detachably hold the umbilical catheter 60 outside the shield 20. Each of the clips 940a, 940b has a first clip portion 944 and a second clip portion 946. The first and second clip portions 944, 946 are separated from each other by a distance to define a clip cavity 948 therebetween. The clip cavity 948 is sized such that the umbilical catheter 60 can be frictionally pushed therein. In the illustrated embodiments, the clip cavity 948 has a first width at the outermost part of the clip 940, and a second width larger than the first width at an inner part of the clip 940. With such configuration, the umbilical catheter 60 will experience a higher friction when initially being pushed radially into the clip cavity 948 of the clip, and once the umbilical catheter 60 passes the outermost part of the clip 940, the umbilical catheter 60 will be accommodated in the inner part of the clip with the larger second width. In some cases, when the umbilical catheter 60 is accommodated in the inner part of the clip 940, the umbilical catheter 60 may experience no clamping force by the clip portions 944, 946. In other cases, the umbilical catheter 60 may experience a slight clamping force by the clip portions 944, 946 that is less compared to the clamping force when the umbilical catheter 60 is being pushed into the clip 940 at the outer most part of the clip 940. In other embodiments, instead of the clip cavity 948 having a larger width at an inner part of the clip 940 compared to the outer part of the clip 940, the clip cavity 948 may have a uniform width extending from the outer part of the clip 940 to an inner part of the clip 940. In further embodiments, the clip cavity 948 may have a decreased width at the inner part of the clip 940 compared to the outer part of the clip 940. Although two clips 940a, 940b are shown, in other embodiments, there may be only one clip 940, or more than two clips 940.

It should be noted that the clip 940 is not limited to the configuration shown, and may have other configurations in other embodiments. For example, instead of having two opposite portions for frictionally grasping the umbilical catheter 60, the clip 940 may include more than two portions (e.g., three portions) that circumferentially engage with different circumferential parts of the umbilical catheter 60.

Also, in the illustrated embodiments, the shield 20 includes a circumferentially disposed spooling groove 942 for accommodating a segment of the umbilical catheter 60 while the segment of the umbilical catheter 60 is wrapped around the shield at the spooling groove 942. The spooling groove 942 may be partially or completely circumferentially disposed around the shield 20. Although only one spooling groove 942 is shown, in other embodiments, the shield 20 may have multiple spooling grooves 942. For example, there may be a first spooling groove, and a second spooling groove, wherein the first spooling groove is above the second spooling groove to form a stacked configuration.

In other embodiments, the device 10 may not include any spooling groove. Instead, the umbilical catheter 60 may be wrapped around an exterior surface of the shield 20, with a direction of the umbilical catheter 60 being defined by one or more of the clips 940.

FIGS. 11A-11C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

The shield 20 also has multiple vents 800. The vents 800 may prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a, 940b disposed at different respective sides of the shield 20. The clips 940a, 940b are configured to detachably hold the umbilical catheter 60 outside the shield 20. Although two clips 940a, 940b are shown, in other embodiments, there may be only one clip 940, or more than two clips 940. The features of the clips 940 are similar to those described with reference to FIG. 10A, and therefore will not be repeated here.

Also, in the illustrated embodiments, the shield 20 includes a circumferentially disposed spooling groove 942 for accommodating a segment of the umbilical catheter 60 while the segment of the umbilical catheter 60 is wrapped around the shield at the spooling groove 942. The spooling groove 942 may be partially or completely circumferentially disposed around the shield 20. Although only one spooling groove 942 is shown, in other embodiments, the shield 20 may have multiple spooling grooves 942. For example, there may be a first spooling groove, and a second spooling groove, wherein the first spooling groove is above the second spooling groove to form a stacked configuration.

In other embodiments, the device 10 may not include any spooling groove. Instead, the umbilical catheter 60 may be wrapped around an exterior surface of the shield 20, with a direction of the umbilical catheter 60 being defined by one or more of the clips 940.

Unlike the embodiments shown in FIG. 10A, the shield 20 in the embodiments of FIGS. 11A-11C does not have the tubular structure 62 at the top of the shield. No stabilizing structure is needed at the top of the shield 20 because the umbilical catheter 60 can be stabilized with respect to the shield 20 by holding the catheter 60 with the clip 920 (with a length of the segment of the catheter 60 between the clip 920 and the opening 50 being as short as possible), by wrapping the umbilical catheter 60 around the spooling groove 924, or by a combination of both.

In addition, unlike the embodiments shown in FIG. 10A, the inner part of the clip cavity 948 in the embodiments of FIGS. 11A-11C is much larger, thereby allowing multiple segments of the umbilical catheter 60 to be placed therein when the umbilical catheter 60 is wrapped around the shield 20 multiple times.

Also, unlike the embodiments shown in FIG. 10A, the spooling groove 942 shown in the embodiments of FIGS. 11A-11C is deeper, thereby allowing the umbilical catheter 60 to be wrapped around the shield 20 multiple times within the spooling groove 942.

In any of the embodiments described herein, the device 10 may have more than one spooling groove 942 for allowing the umbilical catheter 60 to wrap around the shield 20. For example, FIGS. 12A-12C illustrate another device 10 for protecting an umbilical stump-catheter interface, particularly showing the umbilical stump device 10 having multiple spooling grooves. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

In the illustrated embodiments, the shield 20 includes a first circumferentially disposed spooling groove 942a for accommodating a segment of the umbilical catheter 60 while the segment of the umbilical catheter 60 is wrapped around the shield at the spooling groove 942a. The shield 20 also includes a second circumferentially disposed spooling groove 942b for accommodating a segment of the umbilical catheter 60 while the segment of the umbilical catheter 60 is wrapped around the shield at the spooling groove 942b. The first spooling groove 942a is above the second spooling groove 942b to form a stacked configuration. Each of the spooling grooves 942a, 942b may be partially or completely circumferentially disposed around the shield 20. Although two spooling grooves 942a, 942b are shown, in other embodiments, the shield 20 may have only one spooling groove, or more than two spooling grooves 942.

In other embodiments, the device 10 may not include any spooling groove. Instead, the umbilical catheter 60 may be wrapped around an exterior surface of the shield 20, with a direction of the umbilical catheter 60 being defined by one or more of the clips 940.

The shield 20 also has multiple vents 800. The vents 800 may prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a-940d disposed at different respective sides of the shield 20. The clips 940a-940d are configured to detachably hold the umbilical catheter 60 outside the shield 20. The clips 940 are similar to that described in previous embodiments, except that the opening between the clip portions is made smaller to form a very narrow slit. In some cases, the slit has a zero dimension so that the two clip portions at the exterior portion of the clip 940 abut against each other. This configuration is advantageous because once the catheter 60 is pushed through the slit, and is placed in the larger opening at the inner part of the clip 940, the exterior part of the clip 940 where the slit is defined will prevent the catheter 60 from falling out of the clip 940.

FIGS. 13A-13C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

In the illustrated embodiments, the shield 20 of the device 10 also includes a plurality of clips 940a-940d disposed at different respective sides of the shield 20. The clips 940a-940d are configured to detachably hold the umbilical catheter 60 outside the shield 20. Each of the clips 940a-940d has a first clip portion 944, a second clip portion 946, and a third clip portion 950. The first and second clip portions 944, 946 are separated from each other by a distance to define a first clip cavity 948a therebetween. The second and third clip portions 946, 950 are separated from each other by a distance to define a second clip cavity 948b. The clip cavity 948a/948b is sized such that the umbilical catheter 60 can be frictionally pushed therein. In the illustrated embodiments, the clip cavity 948a/948b has a first width at the outermost part of the clip 940, and a second width larger than the first width at an inner part of the clip 940. With such configuration, the umbilical catheter 60 will experience a higher friction when initially being pushed radially into the clip cavity 948a/948b of the clip, and once the umbilical catheter 60 passes the outermost part of the clip 940, the umbilical catheter 60 will be accommodated in the inner part of the clip with the larger second width. In some cases, when the umbilical catheter 60 is accommodated in the inner part of the clip 940, the umbilical catheter 60 may experience no clamping force by the clip portions 944, 946, or by the clip portions 946, 950 (depending whether the clip cavity 948a or the clip cavity 948b is being used). In other cases, the umbilical catheter 60 may experience a slight clamping force by the clip portions 944, 946, or by the clip portions 946, 950 that is less compared to the clamping force when the umbilical catheter 60 is being pushed into the clip 940 at the outer most part of the clip 940. In other embodiments, instead of the clip cavity 948a/948b having a larger width at an inner part of the clip 940 compared to the outer part of the clip 940, the clip cavity 948a/948b may have a uniform width extending from the outer part of the clip 940 to an inner part of the clip 940. In further embodiments, the clip cavity 948a/948b may have a decreased width at the inner part of the clip 940 compared to the outer part of the clip 940. Although four clips 940a-940d are shown, in other embodiments, there may be fewer than four clips 940, or more than four clips 940.

In the illustrated embodiments, each clip 940 has multiple stacked slots 948 for allowing a user to couple the umbilical catheter 60 to a selected one of the slots 948, and/or for allowing a user to wrap the umbilical catheter 60 around the shield 20 multiple times. In other embodiments, the number of slots 948 in each clip 940 may be more than two (e.g., three, four, etc.). Also, it should be noted that the stacked slots 948 feature is not limited to the embodiments of FIGS. 13A-13C, and that other embodiments described herein may optionally include the stacked slots feature.

The shield 20 also has multiple vents 800. The vents 800 may prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

Also, in the illustrated embodiments, the shield 20 includes a circumferentially disposed spooling groove 942 for accommodating a segment of the umbilical catheter 60 while the segment of the umbilical catheter 60 is wrapped around the shield at the spooling groove 942. The spooling groove 942 may be partially or completely circumferentially disposed around the shield 20. Although only one spooling groove 942 is shown, in other embodiments, the shield 20 may have multiple spooling grooves 942. For example, there may be a first spooling groove, and a second spooling groove, wherein the first spooling groove is above the second spooling groove to form a stacked configuration.

In other embodiments, the device 10 may not include any spooling groove. Instead, the umbilical catheter 60 may be wrapped around an exterior surface of the shield 20, with a direction of the umbilical catheter 60 being defined by one or more of the clips 940.

In any of the embodiments described herein, the device 10 may optionally further include a top clip for detachably securing the umbilical catheter 60 at a top cover of the shield 20. For example, FIGS. 14A-14C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

In the illustrated embodiments, the device 10 also includes a top clip 960 located at the upper portion of the shield 20 for detachably securing the umbilical catheter 60 relative to the shield 20. The clip 960 includes a first clip portion 962 and a second clip portion 964. The first and second clip portions 962, 964 are separated from each other by a distance to define a slot 966. The slot 966 is sized so that the umbilical catheter 60 may be frictionally pushed therein and be clamped by the first and second clip portions 962, 964. The top clip 960 is advantageous because it not only secures the umbilical catheter 60 relative to the top portion (cover) of the shield 20, but it also directs the umbilical catheter 60 towards a bottom portion of the shield 20 where the clips 940a-940d are located, so that after a first segment of the umbilical catheter 60 is secured by the top clip 960, the next segment of the umbilical catheter 60 may be secured by one of the clips 940a-940d. As shown in FIG. 14C, the slot 966 is oriented at an angle 970 that is 90° from a direction of the slot 901. In other embodiments, the angle 970 may be more than 90°. Having the angle 970 to be 90° or more is advantageous because it reduces the risk that the umbilical catheter 60 will move out of the slot 901 and become loose.

In other embodiments, the first and second clip portions 962, 964 do not frictionally clamp the umbilical catheter 60. Instead, the first and second clip portions 962, 964 are sufficiently spaced apart so that they do not clamp against the umbilical catheter 60. In such case, the top clip 960 functions to guide the umbilical catheter 60 towards a desired direction. Thus, as used in this specification, the term "clip" is not necessarily limit to a structure that grasp or grip an object (e.g., catheter), and may refer to any structure that accommodates, guide, abut, or touches the object (e.g., catheter).

Figure 19A:
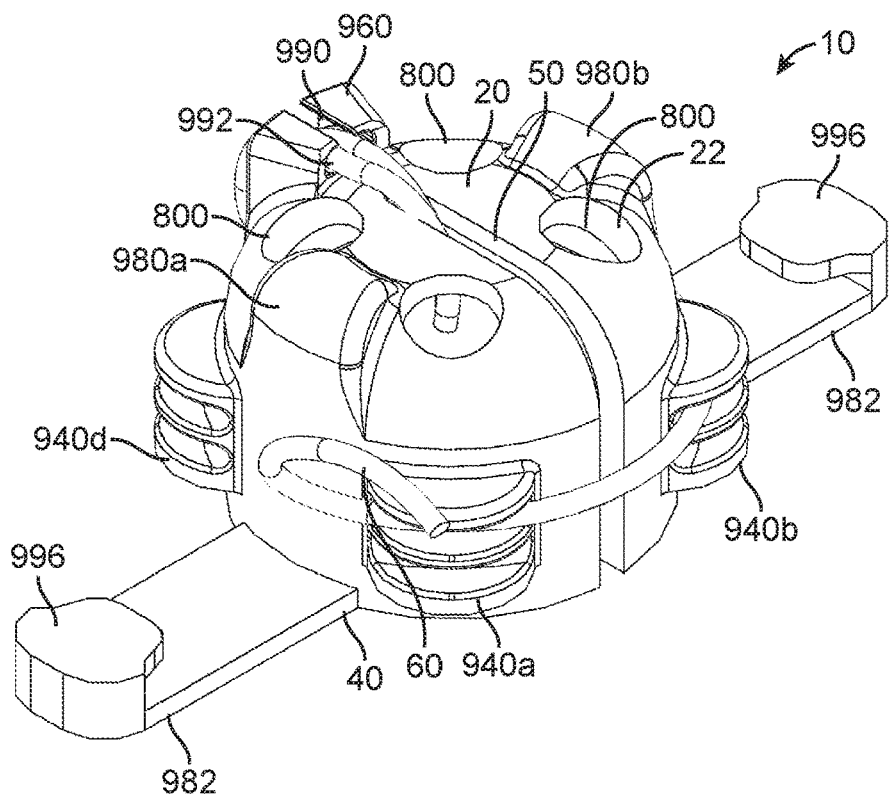
FIG. 19A illustrates a device for protecting umbilical stump-catheter interface, particularly showing the device being used with one catheter.

For example, in other embodiments, the clip 960 may have a configuration like that shown in FIG. 19A, which includes a narrow slot 990 and a larger slot 992 (larger than slot 990). In this configuration, the catheter 60 may first be pushed through the narrow slot 990. Once the catheter 60 is contained in the larger slot 992, the portions defining the narrow slot 990 (due to its width being narrower than a width of the catheter 60) will prevent the catheter 60 from escaping larger slot 992.

Although only one top clip 960 is shown in FIG. 14A, in other embodiments, there may be multiple top clips 960 disposed at the upper portion of the shield 20 for allowing a user to selectively pick to secure the umbilical catheter 60.

The shield 20 also has multiple vents 800. The vents 800 may prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a-940d disposed at different respective sides of the shield 20. The clips 940a-940d are configured to detachably hold the umbilical catheter 60 outside the shield 20. The clips 940a-940d are similar or the same as those described with reference to FIGS. 12A-12C and 13A-13C, and therefore will not be described again. Although four clips 940a-940d are shown, in other embodiments, there may be fewer than four clips 940, or more than four clips 940.

In other embodiments, the device 10 of FIGS. 14A-14C may include one or more spooling groove(s) 942 as similarly described with other embodiments herein.

In any of the embodiments described herein, the device 10 may optionally further include two or more pinching protrusions (e.g., taps) for allowing a user to grasp the device 10. For example, FIGS. 15A-15C illustrate another device 10 for protecting an umbilical stump-catheter interface. The device 10 includes a shield 20 having a wall 22 that defines a cavity 24 for accommodating an umbilical stump. The shield 20 further includes a base 40 for attachment to a patient. In some cases, the base 40 may include an adhesive that allows the base 40 to be attached to the patient. The device 10 includes an opening 50 at the shield 20 for allowing an umbilical catheter 60 to extend therethrough. As shown in the figures, the opening 50 is located at a top of the shield 20, and extends to a side of the shield 20, thereby defining a linear slot at the side of the shield 20. This configuration is advantageous because it allows the shield 20 to be placed around the umbilical catheter 60 by sliding the catheter 60 through the slot at the side of the shield 20. The shield 20 can then be slid down to cover the umbilical stump.

In the illustrated embodiments, the device 10 also includes a first pinching protrusion 980a and a second pinching protrusion 980b located on respective opposite sides from each other and at the upper portion of the shield 20. The pinching protrusions 980a, 980b are configured for allowing a user to grasp the device 10 using fingers. In other embodiments, there may be more than two pinching protrusions. Also, in other embodiments, the pinching protrusions 980 may be located at other areas at the shield 20.

In the illustrated embodiments, the device 10 also includes a top clip 960 located at the upper portion of the shield 20 for detachably securing the umbilical catheter 60 relative to the shield 20. The clip 960 is similar to or the same as the clip 960 described with reference to FIGS. 14A-14C, and therefore will not be described again. Although only one top clip 960 is shown, in other embodiments, there may be multiple top clips 960 disposed at the upper portion of the shield 20 for allowing a user to selectively pick to secure the umbilical catheter 60.

The shield 20 also has multiple vents 800. The vents 800 may prevent a "bio-dome" like effect within the cavity of the shield 20. The vents 800 may be sized and/or positioned at certain parts of the shield 20, so that the vents 800 can allow some air exchange through the wall of the shield 20, while still allowing the shield 20 to protect the umbilical stump by shielding off at least some bacteria. In other embodiments, the shield 20 may have only one vent 800.

In the illustrated embodiments, the shield 20 of the device 10 also includes a plurality of clips 940a-940d disposed at different respective sides of the shield 20. The clips 940a-940d are configured to detachably hold the umbilical catheter 60 outside the shield 20. The clips 940a-940d are similar or the same as those described with reference to FIGS. 12A-12C and 13A-13C, and therefore will not be described again. Although four clips 940a-940d are shown, in other embodiments, there may be fewer than four clips 940, or more than four clips 940.

In other embodiments, the device 10 of FIGS. 15A-15C may include one or more spooling groove(s) 942 as similarly described with other embodiments herein.

Also, as shown in FIGS. 15A-15C, the base 40 of the device 10 may include a plurality of flanges 982a, 982b extending laterally from sides of the shield 20. The flanges 982a, 982b may include adhesive at the underneath surfaces for attachment to a patient. Additionally, or alternatively, each of the flanges 982a, 982b may be taped to the patient using medical tape that extends across the top surface of the flange 982a/982b. The flanges 982a, 982b are advantageous because they provide an increased adhesive area for attachment to the patient, which provides a more secured attachment mechanism. Additionally, or alternatively, the flanges may be taped down to a "safe" adhesive (as described previously to allow for better securement of the device while ensuring that only a "safe" adhesive interfaces with the skin.

Although only two flanges 982 are shown, in other embodiments, there may be more than two flanges 982. For example, FIGS. 16A-16C illustrates a variation of the device 10 that includes three flanges 982a-982c disposed circumferentially around the shield 20.

Also, it should be noted that the flanges 982 are not limited to having rectangular shape like that shown in FIGS. 15-16, and that each of the flanges 982 may have other shapes in other embodiments. For example, in other embodiments, each of the flanges 982 may have a curvilinear shape like that shown in FIG. 17, or a T-shape like that shown in FIG. 18. In addition, in any of the embodiments described herein, a flange 982 may have an anchor (e.g., along a side of the flange 982) for preventing or reducing the risk of a tape being detached from the flange 982. In particular, during use of the device 10, a tape may be used to tape down the flange 982 relative to the patient, while the tape is placed underneath the anchor at the flange 982. The anchor functions to prevent the tape from being pulled upward from the flange 982.

It should be noted that the flange feature is not limited to the embodiments shown in FIGS. 15-18, and it may be included in any of the other embodiments described herein.

Also, in any of the embodiments described herein (e.g., those described in FIGS. 1-17), the device 10 may optionally further include an exterior surface configured for allowing a user to write on. For example, a top portion (e.g., a cover) of the shield 20 may have an exterior surface that forms a dedicated area for allowing a user to write thereon. The dedicated area may comprise a paper, which allows the user to write thereon using pencil or pen. Alternatively, the dedicated area may comprise a plastic sheet, which allows the user to write thereon using a marker. Also, in some embodiments, the dedicated area may comprise a sheet (paper, plastic, etc.) that is removably attached to the shield 20.

Furthermore, in any of the embodiments described herein (e.g., those described in FIGS. 1-17), the device 10 may be made from different materials. For example, a first portion of the shield 20 may be made from a first material, and a second portion of the shield 20 may be made from a second material that is different from the first material. In some cases, the clip(s) 940 and/or the clip(s) 960 may be made from a first material having a first durometer, and another portion of the shield 20 (e.g., the body defining the cavity 24) may be made from a second material having a second durometer, wherein the first durometer is higher than the second durometer.

Also, in any of the embodiments described herein (e.g., those described in FIGS. 1-17), instead of or in addition to, having the opening 50 at the top of the device 10, the device 10 may include an opening at another part of the device 10. For example, in other embodiments, the device 10 may include an opening at a side of the device 10, or at a location that is offset from a center at the top of the device 10.

Figure 19B:
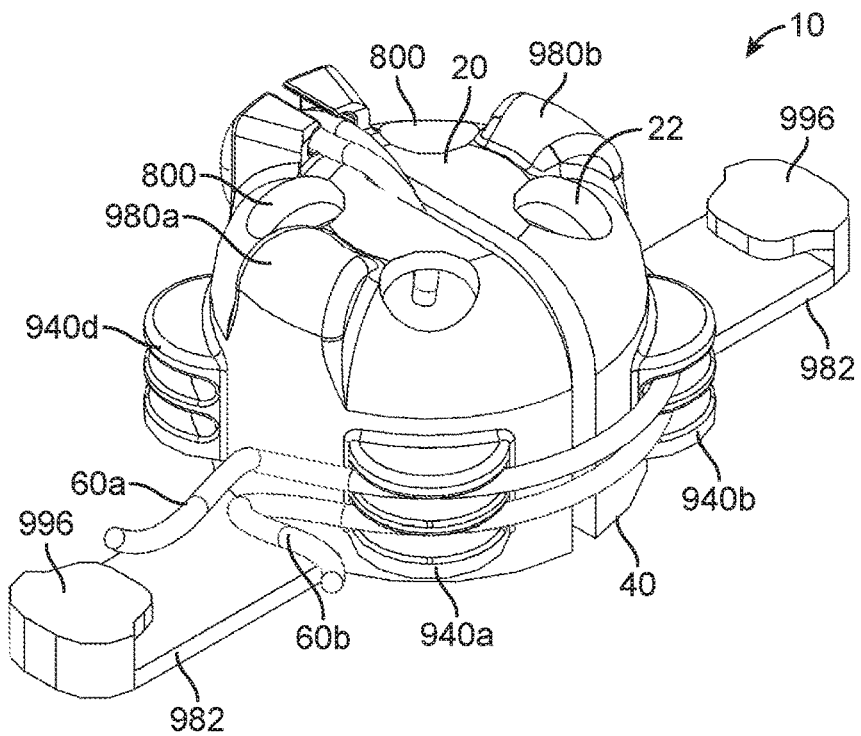
FIG. 19B illustrates a device for protecting umbilical stump-catheter interface, particularly showing the device being used with two catheters.

In the above embodiments, the device 10 is illustrated as being used with one catheter. In any of the embodiments described herein (e.g., those described in FIGS. 1-17), the device 10 may have multiple clips for holding different catheters. For example, the device 10 may have a first clip for holding a first catheter, and a second clip for holding a second catheter. Thus, the device 10 may selectively be used with one or more catheters. FIG. 19A illustrates another device 10 for protecting an umbilical stump-catheter interface, particularly showing the device 10 being used with one catheter 60. However, the same device 10 may also be used with two (or more) catheters. As shown in FIG. 19B, the device 10 is being used with two catheters 60a, 60b. In some cases, the catheters may have different sizes. Thus, in some embodiments, the clips may have different respective sizes. For example, the first clip may have a first catheter slot, and the second clip may have a second catheter slot, wherein the first catheter slot has a dimension that is different from a dimension of the second catheter slot. In other embodiments, the clips may have the same size (e.g., the catheter slots in the clips may have the same size). In further embodiments, the device 10 may have at least three clips for holding three different respective catheters. In any of the embodiments described herein, two or more of the clips may be integrated together as a single component.

Also, as discussed, in some cases, the flanges 982 of the device 10 may be taped down to a patient using a tape. In any of the embodiments described herein, the device 10 may optionally include one or more anchors for preventing or reducing the risk of detachment of the tape from the patient. For example, as shown in the embodiments of FIG. 19A or 19B, each flange 982 may include an anchor 996 at a side of the flange 982. During use, a tape may be placed under the anchor 996 and may be used to tape the flange 982 onto a patient. Because the anchor 996 is above the tape, it functions as an anchor that assists the tape in maintaining its position with respect to the patient.

In addition, in any of the embodiments described herein (e.g., those described in FIGS. 1-17), the device 10 may optionally further include a color-coding and/or labeling. For example, the color coding or labeling may indicate whether a catheter is a venous catheter or an arterial catheter, length of catheter in the patient, etc. In one implementation, the device 10 may include a surface for allowing a nurse or physician to write on. Also, in some embodiments, the labeling may include a single letter indicating whether a catheter is a venous catheter (e.g., letter "V") or an arterial catheter (e.g., letter "A"). Furthermore, in some cases, the labeling may include a number code indicating a length of a catheter.

Furthermore, in any of the embodiments described herein (e.g., those described in FIGS. 1-17), the device 10 may have a cross sectional dimension (e.g., width of shield portion of the device 10 excluding the clips 940 and flanges 982) that is anywhere from 0.5 inch to 5 inches, and more preferably from 0.5 to 3 inches, and more preferably from 0.5 to 2 inches, and even more preferably from 0.5 to 1.5 inches (e.g., 1 inch). In other embodiments, the device 10 may have a cross sectional dimension that is larger than 5 inches. Also, in any of the embodiments described herein, the device 10 may have a wall thickness that is anywhere from 0.02 inch to 0.5 inch, and more preferably from 0.05 to 0.3 inch, and even more preferably from 0.06 to 0.1 inch.

In any of the embodiments described herein (e.g., those described in FIGS. 1-17), the device 10 may be made from a molding process. For example, injection molding, compressing molding, etc., may be used to form part(s) or an entirety of the device 10. In some cases, different molding processes may be used to form different parts of the device 10, and the parts may then be subsequently secured to each other (e.g., using an adhesive, glue, etc.). Various materials may be used to form the device 10. By means of non-limiting examples, the device 10 may be formed from thermoplastic material(s), elastomer(s), polymer(s), etc.

In any of the embodiments described herein, the spooling groove(s) is optional, and the device 10 may not include any spooling groove. For example, in any of the embodiments that includes a spooling groove, such spooling groove may be replaced with one or more clips. The clip(s) is configured to both hold the catheter and to define a position and direction of travel for the catheter.

In any of the embodiments described herein (e.g., those described in FIGS. 1-17), the device 10 may include an antimicrobial component. For example, the device 10 itself may be made from an antimicrobial material. In one implementation, the base of the device 10 includes an antimicrobial material. Alternatively, the entire device 10 may include the antimicrobial material. In some cases, the device 10 may include a ultraviolet (UV) light source coupled to the shield 20 for projecting a UV light towards the stump 30. In further embodiments, the device 10 may include silver, gel, etc. that provides antimicrobial action.

In any of the embodiments described herein (e.g., those described in FIGS. 1-17), the shield 20 may be configured to deform, bend, or collapse in response to a compression force that is less than 1 lb, and more preferably less than 0.5 lb, and even more preferably less than 0.3 lb. This configuration is advantageous because it allows the baby using the device 10 to be in various positions, such as in a facedown position. In particular, if the baby is lying on his/her belly, the device 10 will deform, bend, or collapse so that the device 10 will not be applying an uncomfortable force against the baby, while the position of the catheter relative to the device 10 remains fixed.

In any of the embodiments described herein (e.g., those described in FIGS. 1-17), the device 10 may further include a manual control mechanism (e.g., a clip, a knob, a pincher, etc.) configured to shut the catheter so that fluid flow in the catheter can be stopped when desired. The manual control mechanism may be located at an exterior surface of the shield 20, at the base, or at any of other locations (e.g., at the device-catheter interface). In one implementation, a clip or a mechanism similar to a wingnut/bolt that is used to tighten may be provided at the device-catheter interface for shutting the catheter.

In any of the embodiments described herein (e.g., those described in FIGS. 1-17), the device 10 may further include a position monitoring device for monitoring a position of the catheter with respect to the device 10 (e.g., the shield 20 of the device 10). For example, the position monitoring device may be a marking at the catheter to indicate its position relative to the shield 20. If the position has changed so that the marking on the catheter is further from the shield 20, then it can be inferred that the catheter has moved outward from the patient. Thus, the position monitoring device functions to monitor the depth of the catheter outside of the shield 20. In other embodiments, the position monitoring device may include markers on the catheter, and a camera for viewing the markers on the catheter. Also, in further embodiments, similar techniques may be employed to monitor the position of the catheter with respect to the patient or to the umbilical stump.

In some embodiments, different sizes of the device 10 may be provided. For example, there may be three standard sizes of the device 10, with the larger size being more suitable for larger patient, and the smaller size being more suitable for smaller patient.

In any of the embodiments described herein, if the device 10 includes multiple clips for holding different catheters, the clips may be color coded. For example, a first clip may have a first color, and a second clip may have a second color that is different from the first color. Also, if the device 10 includes a clip that is configured to hold multiple catheters, different portions of the clip may be color coded. For example, a first portion of the clip may define a space for accommodating a first catheter, and a second portion of the clip may define another space for accommodating a second catheter, wherein the first portion and the second portion may have different respective colors.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A device for protecting an umbilical stump-catheter interface, comprising:
a shield having a wall that defines a cavity for accommodating an umbilical stump, the wall configured to be spaced from an umbilical stump when the umbilical stump is accommodated in the cavity, wherein the shield further includes a base for coupling to a patient;
an opening at the shield for allowing an umbilical catheter to extend therethrough; and
a slot at a side of the shield, the slot configured to allow the shield to be placed around the umbilical catheter;
wherein the shield comprises a first clip configured to hold the umbilical catheter by frictional grasping; and
wherein the first clip is made from a first material and has a first stiffness, and wherein another part of the shield is made from a second material and has a second stiffness, the first stiffness being higher than the second stiffness.

2. The device of claim 1, wherein the shield comprises a portion configured to hold the umbilical catheter by frictional grasping.

3. The device of claim 1, wherein the shield has a first shield portion and a second shield portion that is moveable relative to the first shield portion.

4. The device of claim 1, wherein the shield is configured to protect the umbilical stump from bacteria outside the shield and/or from physical contact.

5. The device of claim 1, wherein the base comprises a plurality of flanges extending outward.

6. The device of claim 1, wherein the shield comprises at least two pinching protrusions configured to allow a user to grasp the shield.

7. The device of claim 1, wherein the shield comprises a vent for allowing some air exchange through the wall of the shield.

8. A device for protecting an umbilical stump-catheter interface, comprising:
a shield having a wall that defines a cavity for accommodating an umbilical stump, the wall configured to be spaced from an umbilical stump when the umbilical stump is accommodated in the cavity, wherein the shield further includes a base for coupling to a patient;
an opening at the shield for allowing an umbilical catheter to extend therethrough; and
a slot at a side of the shield, the slot configured to allow the shield to be placed around the umbilical catheter;
wherein the shield comprises one or more spooling grooves at one or more sides of the shield, the one or more spooling grooves configured to accommodate a segment of the umbilical catheter.

9. The device of claim 8, wherein the opening is at a top of the shield.

10. The device of claim 9, wherein the opening at the top of the shield extends to a side of the shield.

11. The device of claim 8, wherein the shield comprises a first clip configured to hold the umbilical catheter by frictional grasping.

12. The device of claim 11, wherein the shield comprises a second clip.

13. The device of claim 12, wherein the first clip is above the second clip to form a stacked configuration.

14. The device of claim 12, wherein the first clip and the second clip are disposed at different respective sides of the shield.

15. The device of claim 12, wherein the second clip is configured to hold the umbilical catheter or another catheter.

16. The device of claim 12, wherein the first clip has a first catheter slot, the second clip has a second catheter slot, the first catheter slot having a dimension that is different from a dimension of the second catheter slot.

17. The device of claim 12, further comprising a third clip, wherein the first clip is configured to hold the umbilical catheter, the second clip is configured to a first additional catheter, and the third clip is configured to hold a second additional catheter or the umbilical catheter.

18. The device of claim 12, wherein the first clip and the second clip are integrated as a single component.

19. The device of claim 8, wherein the shield comprises a first portion having a first stiffness, and a second portion having a second stiffness, the first stiffness being higher than the second stiffness.

20. The device of claim 8, wherein the shield has a top portion, and wherein the shield further comprises a clip at the top portion for holding and/or guiding the umbilical catheter.

21. The device of claim 8, wherein the shield has a top portion, and wherein the shield further comprises at least two pinching protrusions at the top portion for allowing a user to grasp the shield.

22. The device of claim 8, wherein the shield comprises an exterior surface configured for allowing a user to write on.

23. The device of claim 8, wherein the shield comprises a color coding or a labeling.

24. The device of claim 8, wherein the base comprises a T-shape portion, a linear portion, or a curvilinear portion, or a full circumferential portion, extending away from a side of the shield.

25. The device of claim 8, wherein the shield has a first shield portion and a second shield portion that is moveably coupled to the first shield portion, wherein when the second shield portion is in a first position, the umbilical stump is shielded by the shield, and when the second shield portion is in a second position, the umbilical stump is exposed to an environment outside the shield.

26. The device of claim 25, further comprising a mechanical hinge for rotatably coupling the second shield portion to the first shield portion.

27. The device of claim 25, wherein the second shield portion is moveable relative to the first shield portion in a plane that is parallel to the base.

28. The device of claim 8, wherein at least a part of the shield has a dome shape.

29. The device of claim 28, further comprising a tubular structure extending from the dome shape shield, wherein the tubular structure has a channel that extends from the opening.

30. The device of claim 28, wherein the tubular structure is at a top of the dome shape shield.

31. The device of claim 8, further comprising a seal located at or adjacent the opening.

32. The device of claim 8, wherein a majority of the shield is rigid.

33. The device of claim 8, wherein the shield is non-rigid, and is collapsible in response to a compress force that is less than 1 lb.

34. The device of claim 8, further comprising an adhesive at the base for attaching the base to the patient.

35. The device of claim 8, wherein the base includes one or more openings or slots for providing suction to secure the device to the patient.

36. The device of claim 8, further comprising a spring-loaded device for securing the umbilical catheter relative to the device.

37. The device of claim 8, wherein at least a part of the shield is transparent.

38. The device of claim 8, wherein the shield is configured to protect the umbilical stump from bacteria outside the shield and/or from physical contact.

39. The device of claim 8, wherein the shield comprises a vent for allowing some air exchange through the wall of the shield.

40. The device of claim 39, further comprising a permeable or semipermeable cover covering the vent.

41. The device of claim 39, further comprising a cover that can be selectively opened to expose the vent or closed to shut the vent.

42. The device of claim 8, wherein the opening is at a side of the shield.

43. The device of claim 8, wherein the opening is at an upper portion of the shield and is offset from a center of the shield.

44. The device of claim 8, wherein the base, or an entirety, of the shield includes an antimicrobial material.

45. The device of claim 8, further comprising an ultraviolet light source coupled to the shield.

46. The device of claim 8, wherein the shield has a width that is less than 5 inches.

47. The device of claim 8, further comprising a position monitoring device for monitoring a position of the umbilical catheter with respect to the shield, to the patient, or to the umbilical stump.

48. The device of claim 8, wherein the base comprises a plurality of flanges extending outward.

49. The device of claim 48, wherein each flange of the plurality of flanges comprises an anchor opposite the shield.

50. The device of claim 8, further comprising a securement mechanism configured to inhibit movement of the umbilical catheter extending through the opening.

51. The device of claim 8, wherein the shield comprises a first clip configured to hold the umbilical catheter by frictional grasping; and
wherein the first clip is made from a first material and has a first stiffness, and wherein another part of the shield is made from a second material and has a second stiffness, the first stiffness being higher than the second stiffness.

52. The device of claim 8, wherein the shield comprises a circumferentially disposed spooling groove configured to accommodate a segment of the umbilical catheter.

53. The device of claim 8, wherein the shield has a first shield portion and a second shield portion that is moveably coupled to the first shield portion, wherein when the second shield portion is in a first position, the umbilical stump is shielded by the shield, and when the second shield portion is in a second position, the umbilical stump is exposed to an environment outside the shield; and
wherein the device further comprises a securing device for locking the second shield portion relative to the first shield portion when the second shield portion is in the first position.

54. The device of claim 8, wherein the shield has a first shield portion and a second shield portion that is moveably coupled to the first shield portion, wherein when the second shield portion is in a first position, the umbilical stump is shielded by the shield, and when the second shield portion is in a second position, the umbilical stump is exposed to an environment outside the shield; and
wherein the device further comprises a seal located at or adjacent the opening, the seal having a first seal portion that is coupled to the first shield portion, and a second seal portion that is coupled to the second shield portion.

55. The device of claim 8, further comprising a seal located at or adjacent the opening;
wherein the seal has a first seal portion and a second seal portion that cooperates with the first seal portion for securing the umbilical catheter relative to the device.

56. A device for protecting an umbilical stump-catheter interface, comprising:
a shield having a wall that defines a cavity for accommodating an umbilical stump, the wall configured to be spaced from an umbilical stump when the umbilical stump is accommodated in the cavity, wherein the shield further includes a base for coupling to a patient;
an opening at the shield for allowing an umbilical catheter to extend therethrough; and
a slot at a side of the shield, the slot configured to allow the shield to be placed around the umbilical catheter;
wherein the shield comprises a circumferentially disposed spooling groove configured to accommodate a segment of the umbilical catheter.

57. The device of claim 56, wherein the shield comprises a portion configured to hold the umbilical catheter by frictional grasping.

58. The device of claim 56, wherein the shield has a first shield portion and a second shield portion that is moveable relative to the first shield portion.

59. The device of claim 56, wherein the shield is configured to protect the umbilical stump from bacteria outside the shield and/or from physical contact.

60. The device of claim 56, wherein the shield comprises a vent for allowing some air exchange through the wall of the shield.

61. A device for protecting an umbilical stump-catheter interface, comprising:
a shield having a wall that defines a cavity for accommodating an umbilical stump, the wall configured to be spaced from an umbilical stump when the umbilical stump is accommodated in the cavity, wherein the shield further includes a base for coupling to a patient, wherein the shield has a first shield portion and a second shield portion that is moveably coupled to the first shield portion, wherein when the second shield portion is in a first position, the umbilical stump is shielded by the shield, and when the second shield portion is in a second position, the umbilical stump is exposed to an environment outside the shield;
an opening at the shield for allowing an umbilical catheter to extend therethrough; and
a slot at a side of the shield, the slot configured to allow the shield to be placed around the umbilical catheter; and
a securing device for locking the second shield portion relative to the first shield portion when the second shield portion is in the first position.

62. The device of claim 61, wherein the shield comprises a portion configured to hold the umbilical catheter by frictional grasping.

63. The device of claim 61, wherein the shield has a first shield portion and a second shield portion that is moveable relative to the first shield portion.

64. The device of claim 61, wherein the shield is configured to protect the umbilical stump from bacteria outside the shield and/or from physical contact.

65. The device of claim 61, wherein the shield comprises a vent for allowing some air exchange through the wall of the shield.

66. A device for protecting an umbilical stump-catheter interface, comprising:
a shield having a wall that defines a cavity for accommodating an umbilical stump, the wall configured to be spaced from an umbilical stump when the umbilical stump is accommodated in the cavity, wherein the shield further includes a base for coupling to a patient, wherein the shield has a first shield portion and a second shield portion that is moveably coupled to the first shield portion, wherein when the second shield portion is in a first position, the umbilical stump is shielded by the shield, and when the second shield portion is in a second position, the umbilical stump is exposed to an environment outside the shield;
an opening at the shield for allowing an umbilical catheter to extend therethrough; and
a slot at a side of the shield, the slot configured to allow the shield to be placed around the umbilical catheter; and
a seal located at or adjacent the opening, the seal having a first seal portion that is coupled to the first shield portion, and a second seal portion that is coupled to the second shield portion.

67. The device of claim 66, wherein the shield comprises a portion configured to hold the umbilical catheter by frictional grasping.

68. The device of claim 66, wherein the shield has a first shield portion and a second shield portion that is moveable relative to the first shield portion.

69. The device of claim 66, wherein the shield is configured to protect the umbilical stump from bacteria outside the shield and/or from physical contact.

70. The device of claim 66, wherein the shield comprises a vent for allowing some air exchange through the wall of the shield.

71. A device for protecting an umbilical stump-catheter interface, comprising:
a shield having a wall that defines a cavity for accommodating an umbilical stump, the wall configured to be spaced from an umbilical stump when the umbilical stump is accommodated in the cavity, wherein the shield further includes a base for attachment to a patient;
an opening at the shield for allowing an umbilical catheter to extend therethrough; and
a slot at a side of the shield, the slot configured to allow the shield to be placed around the umbilical catheter;
wherein the device further comprises a seal located at or adjacent the opening; and
wherein the seal has a first seal portion and a second seal portion that cooperates with the first seal portion for securing the umbilical catheter relative to the device.

72. The device of claim 71, wherein the shield comprises a portion configured to hold the umbilical catheter by frictional grasping.

73. The device of claim 71, wherein the shield has a first shield portion and a second shield portion that is moveable relative to the first shield portion.

74. The device of claim 71, wherein the shield is configured to protect the umbilical stump from bacteria outside the shield and/or from physical contact.

75. The device of claim 71, wherein the shield comprises a vent for allowing some air exchange through the wall of the shield.

76. A kit comprising:
the device of claim 8; and
one or a combination of two or more of: a scissor, a scalpel, a stopcock, a syringe, a measuring tape, a dilator, a needle, a sterilization material, a catheter, a drape, a sponge, a suture, an umbilical tie, an anesthetic agent, a forceps, a needle holder, a hemostat, a syringe, a bag of sterile saline, and a gauze pad.

77. The kit of claim 76, further comprising a container having a compartment for housing the device, and one or more additional compartment(s) for housing the scissor, the scalpel, the stopcock, the syringe, the measuring tape, the dilator, the needle, the sterilization material, the catheter, the drape, the sponge, the suture, the umbilical tie, the anesthetic agent, the forceps, the needle holder, the hemostat, the syringe, the bag of sterile saline, the gauze pad, and any combination of two or more of the foregoing.

* * * * *